US012755410B2

(12) United States Patent
Liu et al.

(10) Patent No.: US 12,755,410 B2
(45) Date of Patent: Oct. 6, 2026

(54) SYSTEMS AND METHODS FOR AN ENVIRONMENT-AWARE PREDICTIVE MODELING FRAMEWORK FOR HUMAN-ROBOT SYMBIOTIC WALKING

(71) Applicant: Arizona Board of Regents on Behalf of Arizona State University, Tempe, AZ (US)

(72) Inventors: Xiao Liu, Tempe, AZ (US); Geoffrey Clark, Phoenix, AZ (US); Heni Ben Amor, Tempe, AZ (US)

(73) Assignee: Arizona Board of Regents on Behalf of Arizona State University, Tempe, AZ (US)

( * ) Notice: Subject to any disclaimer, the term of this patent is extended or adjusted under 35 U.S.C. 154(b) by 399 days.

(21) Appl. No.: 18/570,521

(22) PCT Filed: Jun. 14, 2022

(86) PCT No.: PCT/US2022/033464
§ 371 (c)(1),
(2) Date: Dec. 14, 2023

(87) PCT Pub. No.: WO2022/266122
PCT Pub. Date: Dec. 22, 2022

(65) Prior Publication Data

US 2024/0289973 A1 Aug. 29, 2024

Related U.S. Application Data

(60) Provisional application No. 63/210,187, filed on Jun. 14, 2021.

(51) Int. Cl.
*A61H 3/00* (2006.01)
*A61F 2/64* (2006.01)
(Continued)

(52) U.S. Cl.
CPC .............. *G06T 7/55* (2017.01); *A61F 2/6607* (2013.01); *A61H 1/0266* (2013.01); *A61H 3/00* (2013.01);
(Continued)

(58) Field of Classification Search
None
See application file for complete search history.

(56) References Cited

U.S. PATENT DOCUMENTS

| | | | | |
|---|---|---|---|---|
| 9,460,339 | B2 * | 10/2016 | Litvak | G06T 7/521 |
| 10,076,425 | B2 * | 9/2018 | Farina | B25J 9/161 |

(Continued)

FOREIGN PATENT DOCUMENTS

| | | | | | |
|---|---|---|---|---|---|
| CN | 120189317 | A * | 6/2025 | | A61B 5/1079 |
| WO | WO-2009131539 | A1 * | 10/2009 | | G06F 3/017 |
| WO | WO-2021076185 | A1 * | 4/2021 | | G06N 3/044 |

OTHER PUBLICATIONS

Au, S.K., "Powered Ankle-Foot Prosthesis Improves Walking Metabolic Economy," IEEE Transactions on Robotics, vol. 25, No. 1, Feb. 2009, 16 pages.

(Continued)

*Primary Examiner* — Ann Hu
(74) *Attorney, Agent, or Firm* — Polsinelli PC

(57) ABSTRACT

An environment-aware prediction and control framework, which incorporates learned environment and terrain features into a predictive model for human-robot symbiotic walking, is disclosed herein. First, a compact deep neural network is introduced for accurate and efficient prediction of pixel-level depth maps from RGB inputs. In turn, this methodology reduces the size, weight, and cost of the necessary hardware, while adding key features such as close-range sensing, filtering, and temporal consistency. In combination with human kinematics data and demonstrated walking gaits, the (Continued)

extracted visual features of the environment are used to learn a probabilistic model coupling perceptions to optimal actions. The resulting data-driven controllers. Bayesian Interaction Primitives, can be used to infer in real-time optimal control actions for a lower-limb prosthesis. The inferred actions naturally take the current state of the environment and the user into account during walking.

8 Claims, 22 Drawing Sheets
(14 of 22 Drawing Sheet(s) Filed in Color)

(51) Int. Cl.

| | |
|---|---|
| ***A61F 2/66*** | (2006.01) |
| ***A61H 1/02*** | (2006.01) |
| ***G06T 7/11*** | (2017.01) |
| ***G06T 7/55*** | (2017.01) |
| ***G06T 17/05*** | (2011.01) |
| *A61F 2/70* | (2006.01) |

(52) U.S. Cl.
CPC .......... *G06T 7/11* (2017.01); *A61F 2002/704* (2013.01); *G06T 2207/10024* (2013.01); *G06T 2207/20016* (2013.01); *G06T 2207/20084* (2013.01)

(56) References Cited

U.S. PATENT DOCUMENTS

| | | | | |
|---|---|---|---|---|
| 11,164,321 | B2 * | 11/2021 | Hsu | G06T 17/20 |
| 12,067,798 | B2 * | 8/2024 | Lopez Mendez | G06V 40/10 |
| 2002/0135581 | A1 * | 9/2002 | Russell | G06T 7/11 345/474 |
| 2003/0120183 | A1 * | 6/2003 | Simmons | A61F 4/00 600/595 |
| 2017/0123487 | A1 * | 5/2017 | Hazra | G06F 3/0482 |
| 2017/0151081 | A1 * | 6/2017 | Feris | A61F 5/0102 |
| 2017/0266019 | A1 * | 9/2017 | Farina | A61F 2/583 |
| 2017/0360578 | A1 | 12/2017 | Shin et al. | |
| 2018/0129284 | A1 | 5/2018 | Davis et al. | |
| 2019/0143517 | A1 | 5/2019 | Yang et al. | |
| 2019/0231220 | A1 | 8/2019 | Refai et al. | |
| 2020/0090408 | A1 * | 3/2020 | Virkar | G06T 15/04 |

OTHER PUBLICATIONS

Amor, Heni Ben, et al., "Interaction Priitives for Human-Robot Cooperation Tasks," IEEE International Conference on Robotics & Automation (ICRA), 2014, 7 pages.
Bhoi, Amlaan, "Monocular Depth Estimation: A Survey," Department of Computer Science, University of Illinois @ Chicago, Jan. 2019, 8 pages.
Campbell, J., et al., "Bayesian Interaction Primitives: A Slam Approach to Human-Robot Interaction," 1st Conference on Robot Learning 2017 (CoRL2017), Mountain View, USA, 9 pages.
Campbell, J., et al., "Learning Interactive Behaviors for Musculoskeletal Robots Using Bayesian Interaction primitives," National Science Foundation and Honda Research Institute, Aug. 2019, 8 pages.
Campbell, J., et al., "Probabilistic Multimodal Modeling for Human-Robot Interaction Tasks," National Science Foundation and Honda Research Institute, Aug. 2019, 9 pages.
Clark, G., et al., "Learning Predictive Models for Ergonomic Control of Prosthetic Devices," 4th Conference on Robot Learning (CoRL 2020), Nov. 2020, 11 pages.
Clark, G., et al., "Predictive Modeling of Periodic Behavior for Human-Robot Symbiotic Walking," IEEE International Conference on Robotics and Automation (ICRA) 2020, 7 pages.
Cui, Y., et al., "Environment-adaptive interaction primitives through visual context for human-robot motor skill learning," Autonomous Robots, 2019, 43:1225-1240, 16 pages.
Dagnelie, Gislin, "Real and virtual mobility performance in simulated prosthetic vision," Journal of Neural Engineering 4 S92, 2007, 11 pages.
Fang, Z., "Towards Good Practice for CNN-Based Monocular Depth Estimation," IEEE Xplore, 2020, 10 pages.
Figueiredo, J., et al., "Daily Locomotion Recognition and Prediction: A Kinematic Data-Based Machine Learning Approach," IEEE Access, vol. 8, Feb. 2020, 13 pages.
Filitchkin, Paul and Katie BYL, "Feature-Based Terrain Classification for LittleDog," IEEE/RSJ International Conference on Intelligent Robots and Systems, Oct. 2012, 6 pages.
Ge, C., et al., "A spiking neural network model for obstacle avoidance in simulated prosthetic vision," Information Sciences 399, Mar. 4, 2017, 30-42, 13 pages.
Geiger, A., et al., "Vision meets robotics: The Kitty dataset," The International Journal of Robotics Research, 32(11) 1231-1237, 2013, 7 pages.
Goodrich, Michael A., and Alan C. Schultz, "Human-Robot Interaction: A Survey," Foundation and Trends in Human-Computer Interaction, vol. 1, No. 3, 2007, 31 pages.
Grimmer, M., et al., "A powered prosthetic ankle joint for walking and running," BioMedical Engineering Online, 2016, 15(Suppl3):141, 16 pages.
Hayhoe, M., et al., "The role of binocular vision in walking," Visual Neuroscience, 2009, 26:73-80, 8 pages.
He, K., et al., "Deep Residual Learning for Image Recognition," IEEE Conference on Computer Vision and Pattern Recognition, 2016, 9 pages.
He, K., et al., "Mask R-CNN," IEEE International Conference on Computer Vision, 2017, 9 pages.
Herr, Hugh, "Exoskeletons and orthoses: classification, design challenges and future directions," Journal of NeuroEngineering and Rehabilitation, Jun. 18, 2009, 9 pages.
"SH-2 Reference Manual", Hillcrest Labs, Document No. 1000-3625, Document Revision: 1.2, May 19, 2017, 83 pages.
Hoover, C.D., "Stair Ascent With a Powered Transfemoral Prosthesis Under Direct Myoelectric Control," IEEE/ASME on Mechatronics, vol. 18, No. 3, Jun. 2013, 10 pages.
Hussein, A., et al., "Imitation Learning: A Survey of Learning Methods," ACM Comput, Surv. 50, 2, Article 21, Apr. 2017, 35 pages.
Ingraham, K.A., et al., "Choosing appropriate prosthetic ankle work to reduce the metabolic cost of individuals with transtibial amputation," Scientific Reports (2018) 8:15303, Oct. 17, 2018, 12 pages.
Islam, M., et al., "Developing Walking Assistants for Visually Impaired People: A Review," IEEE Sensors Journal, vol. 19, No. 8, Apr. 15, 2019, 15 pages.
Khademi, Gholamreza, and Dan Simon, "Convolutional Neural Network for Environmentally Aware Locomotion Mode Recognition of Lower-Limb Amputees," ASME (2019), Jun. 2019, 11 pages.
Khan, Y. N., et al., "High Resolution Visual Terrain Classification for Outdoors Robots," IEEE International Conference on Computer Vision Workshops, 2011, 8 pages.
Kim, H., et al., "Kinematic-based locomotion mode recognition for power augmentation exoskeleton," Internation Journal of Advanced Robotic Systems, Jul. 2017, 14 pages.
Krausz, N.E., et al., "Depth Sensing for Improved Control of Lower Limb Prostheses," IEEE Transactions on Biomedical Engineering, vol. 62, No. 11, Nov. 2015, 12 pages.
Kunzler, M.R., et al., "Should we consider steps with variable height for a safer stair negotiation in older adults?" Work 59 (2018) 15-21, 2018, 8 pages.
Liu, D., et al., "Vision-Assisted Autonomous Lower-Limb Exoskeleton Robot," IEEE Transactions on Systems, Man, and Cybernetics: System, vol. 51, No. 6, Jun. 2021, 12 pages.
Logan, D., et al., "The many roles of vision during walking," Exp Brain Res (2010), Sep. 2010, 206:337-350, 14 pages.
Luo, X, et al., "Consisten Video Depth Estimation," ACM Trans. Graph. 39, 4, Article 71, Jul. 2020, 13 pages.

(56) References Cited

OTHER PUBLICATIONS

Luo, G., et al., "Random forest-based classification and analysis of hemiplegia gait using low-cost depth cameras," Medical & Biological Engineering & Computing, 2020, 58:373-382, 10 pages.
Matthis, J. S., et al., "Gaze and the Control of Foot Placement When Walking in Natural Terrain," Current Biology 28, Apr. 23, 2018, 16 pages.
Maximov, M., et al., "Focus on defocus: bridging the synthetic to real domain gap for depth estimation," IEEE/CVF Conference on Computer Vision and Pattern Recognition (CVPR), 2020, 10 pages.
Mayer, N., et al., "A Large Dataset to Train Convolutional Networks for Disparity, Optical Flow, and Scene Flow Estimation," IEEE Conference on Computer Vision and Pattern Recognition, 2016, 9 pages.
Montgomery, Jana r., and Alena M. Grabowski, Use of a powered ankle—foot prosthesis reduces the metabolic cost of uphill walking and improves leg work symmetry in people with transtibial amputations, J. R. Soc. Interface 15: 20180442, Jun. 14, 2018, 9 pages.
Oh, J., et al., "Comparison of predicted kinetic variables between Parkinson's disease patients and healthy age-matched control using a depth sensor-driven full-body musculoskeletal model," Gait & Posture 76 (2020) 151-156, 6 pages.
Ranjan, A., et al., "Competitive Collaboration: Joint Unsupervised Learning of Depth, Camera Motion, Optical Flow and Motion Segmentation," IEEE/CVF Conference on Computer Vision and Pattern Recognition (CVPR), 2019, 10 pages.
Schonberger, J.L., et al., "Structure-from-Motion Revisited," IEEE Conference on Computer Vision and Pattern Recognition, 2016, 10 pages.
Shultz, A.H., et al., "Running With a Powered Knee and Ankle Prosthesis," IEEE Transactions on Neural Systems and Rehabilitation Engineering, vol. 23, No. 3, May 2015, 10 pages.
Shultz, A.H., et al., "A Unified Controller for Walking on Even and Uneven Terrain With a Powered Ankle Prosthesis," IEEE Transactions on Neural Systems and Rehabilitation Engineering, vol. 26, No. 4, Apr. 2018, 10 pages.
Silberman, N., et al., "Indoor Segmentation and Support Inference from RGBD Images," ECCV 2012, Part V, LNCS 7576, 15 pages.
Simon, A.M., et al., "Configuring a Powered Knee and Ankle Prosthesis for Transfemoral Amputees within Five Specific Ambulation Modes," PLoS ONE 9(6), Jun. 10, 2014, 10 pages.
Skaggs, Steve and Chris Hopper, "Individuals with Visual Impairments: A Review of Psychomotor Behavior," Adapted Physical Activity Quarterly, 1996, vol. 13, 12 pages.
Stolyarov, R., et al., "Accurate Heuristic Terrain Prediction in Powered Lower-Limb Prostheses Using Onboard Sensors," IEEE Transactions on Biomedical Engineering, vol. 68, No. 2, Feb. 2021, 9 pages.
Tucker, et al., "Control strategies for active lower extremity prosthetics and orthotics: a review," Journal of NeuroEngineering and Rehabilitation, 2015, 12:1, 30 pages.
Varol, Huseyin Atakan, Frank Sup, and Michael Goldfarb, "Multiclass Real-Time Intent Recognition of a Powered Lower Limb Prosthesis," IEEE Transactions on Biomedical Engineering, vol. 57, No. 3, Mar. 2010, 10 pages.
Yang, K., et al., "Unifying Terrain Awareness for the Visually Impaired through Real-Time Semantic Segmentation," Sensors 2018, 18, 1506, May 10, 2018, 32 pages.
Zhang, H., et al., "Exploiting temporal consistency for real-time video depth estimation," IEEE/CVF International Conference on Computer Vision (ICCV), 2019, 10 pages.
International Search Report and Written Opinion in corresponding Application No. PCT/US2022/033464 issued Nov. 3, 2022, 14 pages.

* cited by examiner

212

SYSTEMS AND METHODS FOR AN ENVIRONMENT-AWARE PREDICTIVE MODELING FRAMEWORK FOR HUMAN-ROBOT SYMBIOTIC WALKING

CROSS-REFERENCE TO RELATED APPLICATIONS

This is a PCT application that claims benefit to U.S. Provisional Patent Application Ser. No. 63/210,187 filed 14 Jun. 2021, which is herein incorporated by reference in its entirety.

GOVERNMENT SUPPORT

This invention was made with government support under 1749783 awarded by the National Science Foundation. The government has certain rights in the invention.

FIELD

The present disclosure generally relates to human-robot interactive systems, and in particular to a system and associated method for an environment-aware predictive modeling framework for a prosthetic or orthotic joint.

BACKGROUND

Robotic prostheses and orthotics have the potential to change the lives of millions of lower-limb amputees or non-amputees with mobility-related problems for the better by providing critical support during legged locomotion. Powered prostheses and orthotics enable complex capabilities such as level-ground walking and running or stair climbing, while also enabling reductions in metabolic cost and improvements in ergonomic comfort. However, most existing devices are tuned toward and heavily focus on unobstructed level-ground walking, to the detriment of other gait modes—especially those required in dynamic environments. Limitations to the range and adaptivity of gaits has negatively impacted the ability of amputees to navigate dynamic landscapes. Yet, the primary cause of falls is inadequate foot clearance during obstacle traversal during obstacle traversal. In many cases only millimeters decide whether a gait will be safe or whether it will lead to a dangerous contact with the environment. In light of this observation, control solutions are needed to facilitate safe and healthy locomotion over common and frequent barriers such as curbs or stairs. A notable challenge for intelligent prosthetics to overcome is therefore the ability sense and act upon important features in the environment.

Prior work in the field has centered on identifying discrete terrain classes based on kinematics including slopes, stairs, and uneven terrain. Vision systems in the form of depth sensors have recently been utilized in several vision-assisted exoskeleton robots. However, depth sensors with sufficient accuracy at close range are not portable, e.g., Li-DAR, and often prohibitively expensive. There is a current lack of solutions that provide high fidelity depth sensing and portability for use in environment-aware prosthetics.

It is with these observations in mind, among others, that various aspects of the present disclosure were conceived and developed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Corresponding reference characters indicate corresponding elements among the view of the drawings. The headings used in the figures do not limit the scope of the claims.

DETAILED DESCRIPTION

Figure 1:
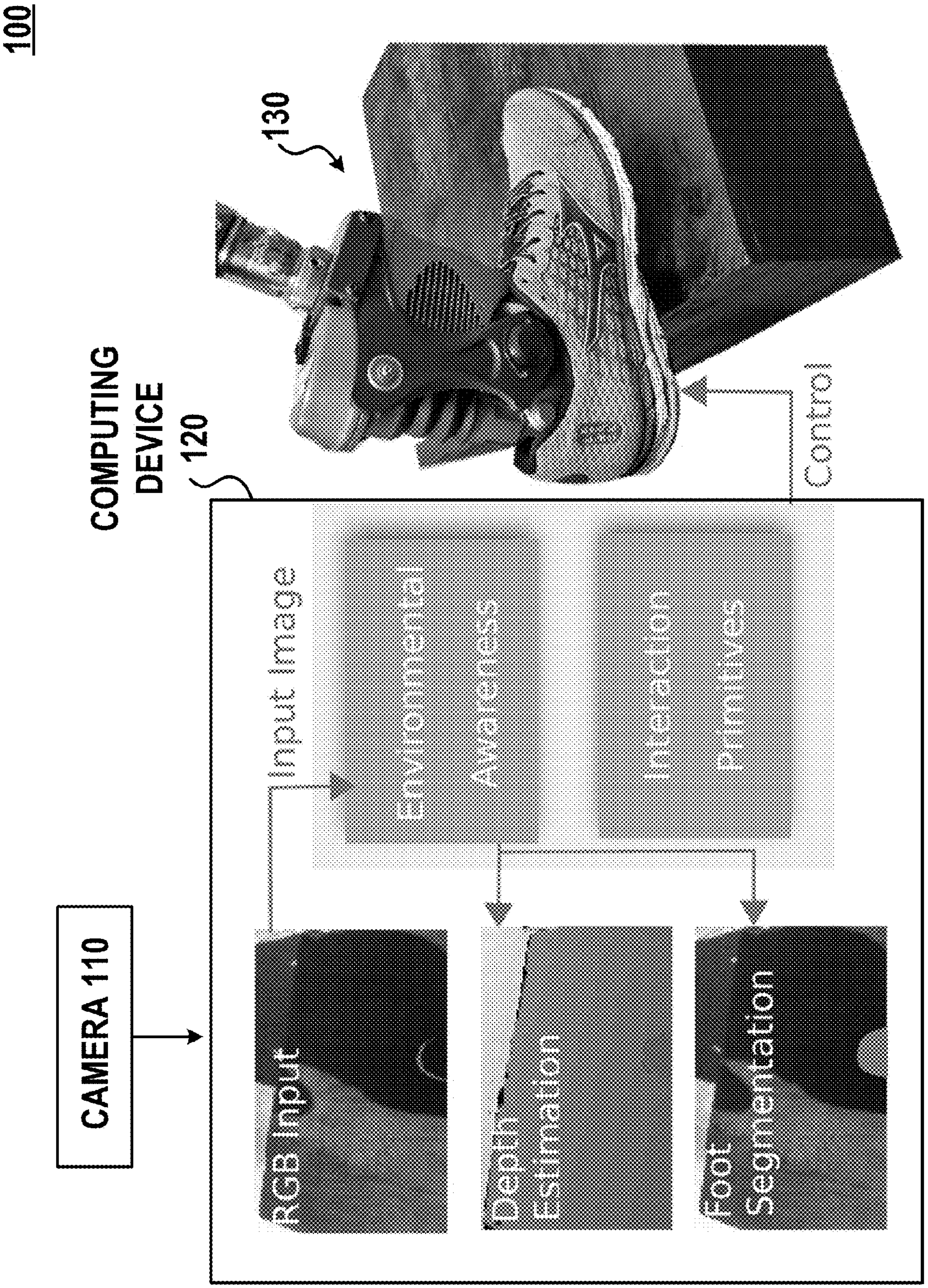
FIG. 1 is a simplified diagram showing a system for environment-aware generation of control signals for a prosthetic or orthotic joint.

Various embodiments of an environment-aware prediction and control system and associated framework for human-robot symbiotic walking are disclosed herein. The system takes a single, monocular RGB image from a leg-mounted camera to generate important visual features of the current surroundings, including the depth of objects and the location of the foot. In turn, the system includes a data-driven controller that uses these features to generate adaptive and responsive actuation signals. The system employs a data-driven technique to extract critical perceptual information from low-cost sensors including a simple RGB camera and IMUs. To this end, a new, multimodal data set was collected for walking with the system on variable ground across 57 varied scenarios, e.g., roadways, curbs, gravel, etc. In turn, the data set can be used to train modules for environmental awareness and robot control. Once trained, the system can process incoming images and generate depth estimates and segmentations of the foot. Together with kinematic sensor modalities from the prosthesis, these visual features are then used to generate predictive control actions. To this end, the system builds upon ensemble Bayesian interaction primitives (enBIP), which have previously been used for accurate prediction in human biomechanics and locomotion. However, going beyond prior work on Interaction Primitives, the present system incorporates the perceptual features directly into a probabilistic model formulation to learn a state of the environment and generate predictive control signals. As a result of this data-driven training scheme, the prosthesis automatically adapts to variations in the ground for mobility-related actions such as lifting a leg to step up a small curb.

Environment-Aware Prediction and Control System

Referring to FIGS. 1-4B, an environment-aware prediction and control system 100 (hereinafter, system 100) integrates depth-based environmental terrain information into a holistic control model for human-robot symbiotic walking. The system 100 provides a prosthetic or orthotic joint 130 in communication with a computing device 120 and a camera 110 that collectively enable the prosthetic or orthotic joint 130 to take environmental surroundings into account when performing various actions. In one example embodiment shown in FIG. 1, the prosthetic or orthotic joint 130 is a powered, electronically assisted prosthetic or orthotic that includes an ankle joint. The prosthetic or orthotic joint 130 can receive one or more control signals from the computing device 120 that dictate movement of various sub-components of the prosthetic or orthotic joint 130. As such, the prosthetic or orthotic joint 130 can be configured to assist a wearer in performing various mobility-related tasks such as walking, stepping onto stairs and/or curbs, shifting weight, etc.

The computing device 120 receives image and/or video data from the camera 110 which captures information about various environmental surroundings and enables the computing device 120 to make informed decisions about the control signals applied to the prosthetic or orthotic joint 130. The computing device 120 includes a processor in communication with a memory, the memory including instructions that enable the processor to implement a framework 200 that receives the image and/or video data from the camera 110 as the wearer uses the prosthetic or orthotic joint 130, extracts a set of depth features from the image and/or video data that indicate perceived spatial depth information of a surrounding environment, and determines a control signal to be applied to the prosthetic or orthotic joint 130 based on the perceived depth features. Following determination of the control signal by the framework 200 implemented at the processor, the computing device 120 applies the control signal to the prosthetic or orthotic joint 130. The present disclosure investigates the efficacy of the system 100 by evaluating how well the prosthetic or orthotic joint 130 performs on tasks such as stepping onto stairs or curbs aided by the framework 200 of the computing device 120. In some embodiments, the camera 110 can be leg-mounted or mounted in a suitable location that enables the camera 110 to capture images of an environment that is in front of the prosthetic or orthotic joint 130. To achieve environmental awareness in human-robot symbiotic walking of the system 100, the following is achieved: (a) perform visual and kinematic data collection from an able-bodied subject, (b) augment the data set with segmented depth features from a trained depth estimation deep neural network, and (c) train a probabilistic model to synthesize control signals to be applied to the prosthetic or orthotic joint 130 given perceived depth features.

The framework 200 implemented at the computing device 120 of system 100 is depicted in FIGS. 2A-2D. The framework 200 is organized into two main sections including: a depth and segmentation module 210 (FIG. 2C) that extracts the set of depth features indicative of spatial depth information of a surrounding environment from an image captured by the camera 110 and performs a foot segmentation task on the image; and a control output module 220 (FIG. 2D) that generates control signals for the computing device 120 to apply to the prosthetic or orthotic joint 130 based on the set of depth features extracted by depth and segmentation module 210 from the image captured by the camera 110. The depth and segmentation module 210 includes a depth estimation network 212 defining a network architecture, with loss functions and temporal consistency constraints that enable the depth and segmentation module 210 to estimate a pixel level depth map from image data captured by the camera 110, while ensuring low noise and high temporal consistency. In some embodiments, the image data captured by the camera 110 includes an RGB value for each respective pixel of a plurality of pixels of the image data, which the depth and segmentation module 210 uses to extract depth features of the surrounding environment. As humans naturally use depth perception to modulate their own movements during mobility-related tasks, the system 100 extends this ability to the prosthetic or orthotic joint 130 by using depth perception to modulate control inputs applied to the prosthetic or orthotic joint 130.

Figure 2A:
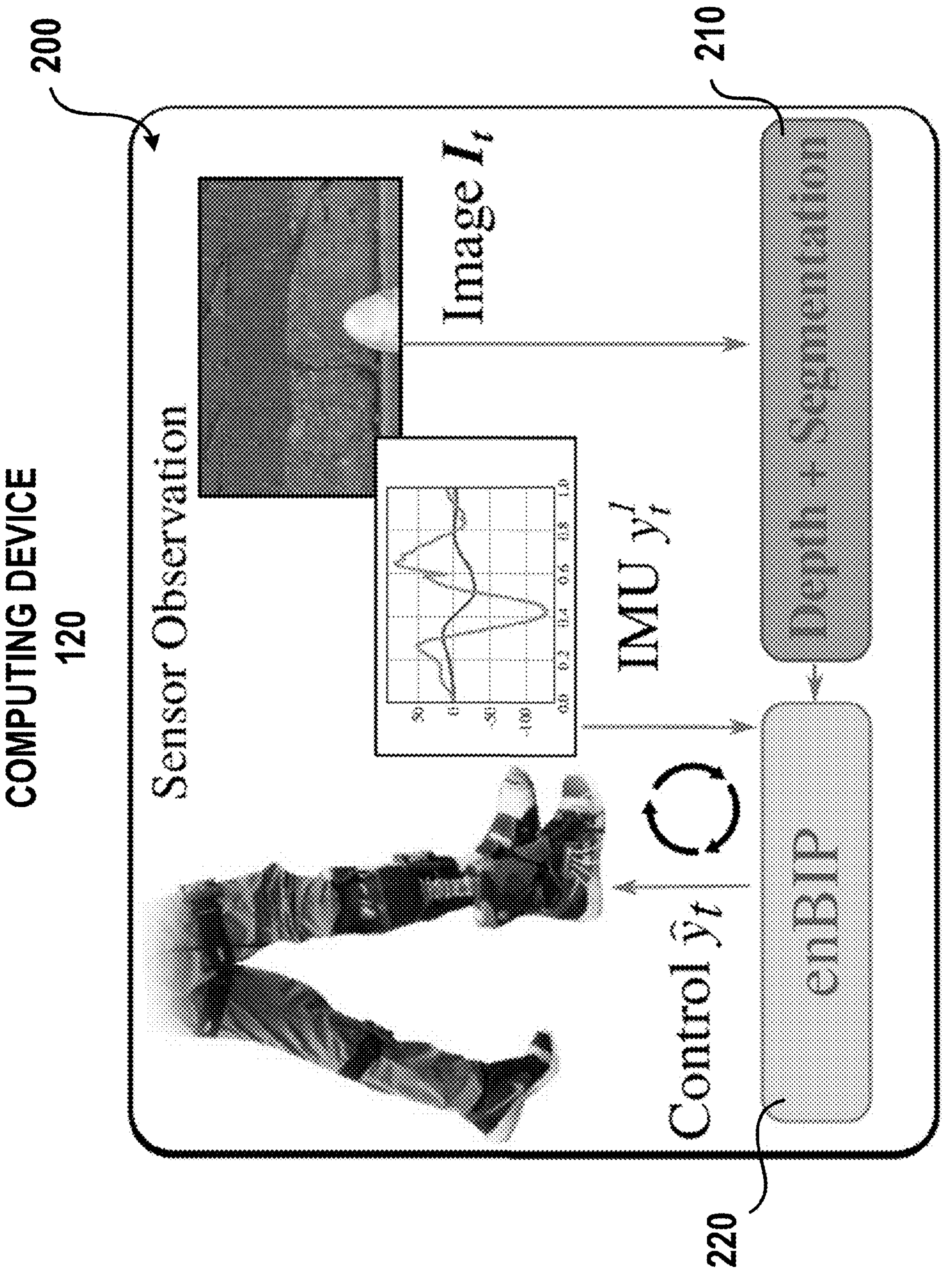
FIGS. 2A and 2B are simplified diagrams showing a framework for generating a control model for the system of FIG. 1.
Figure 2B:
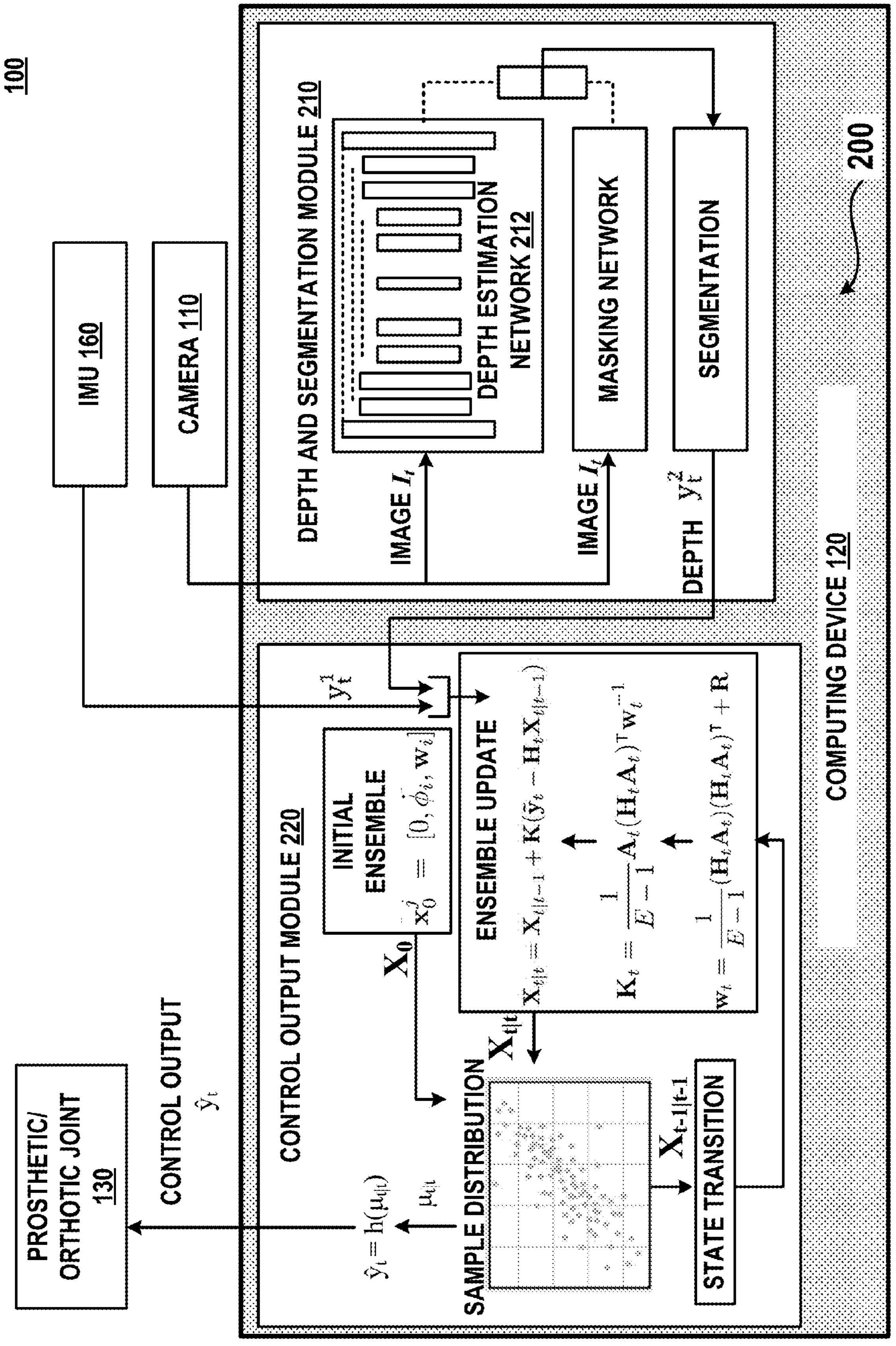
Figure 2C:
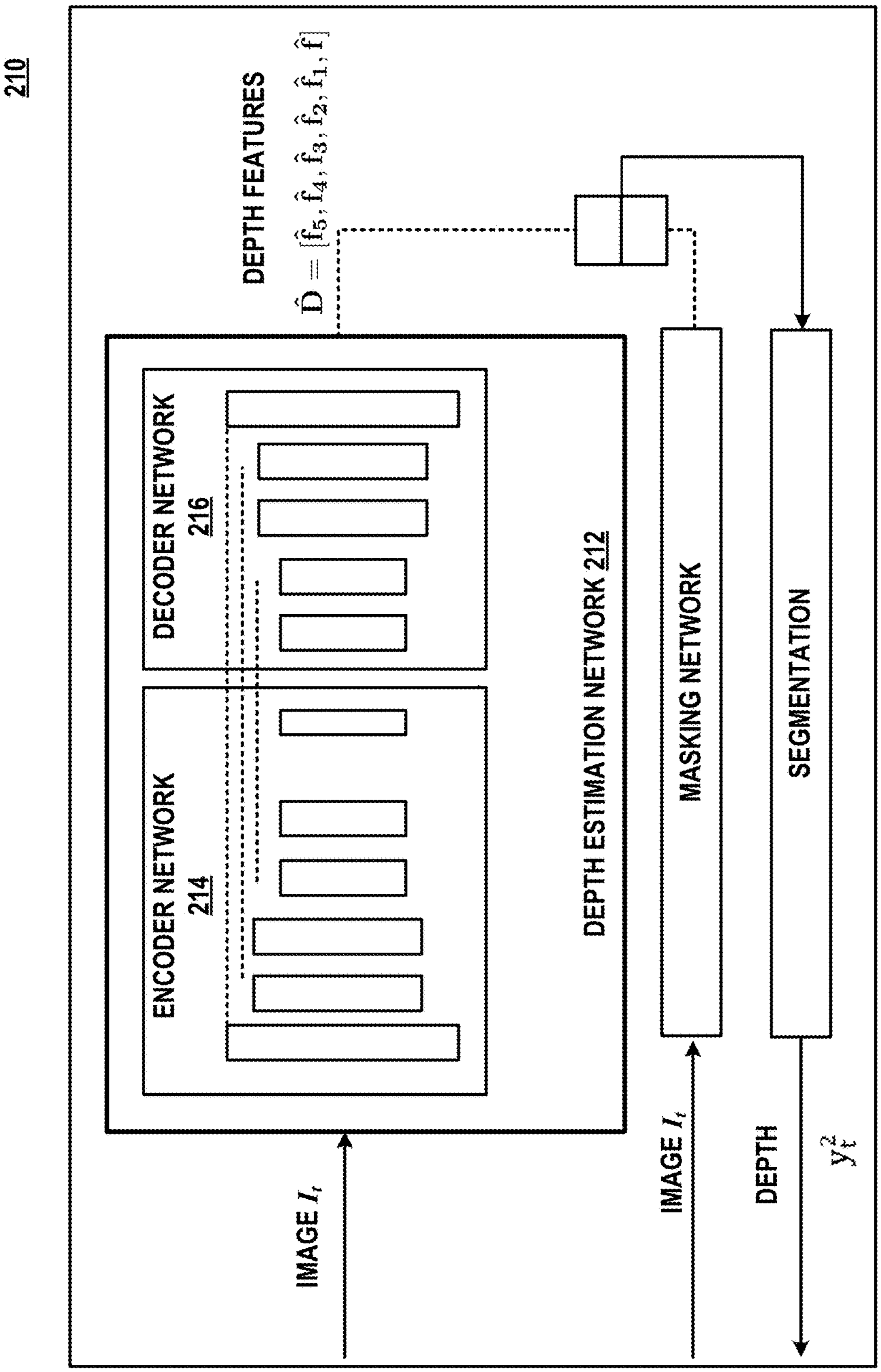
FIG. 2C is a simplified diagram showing a depth and segmentation model for the framework of FIG. 2A.
Figure 2D:
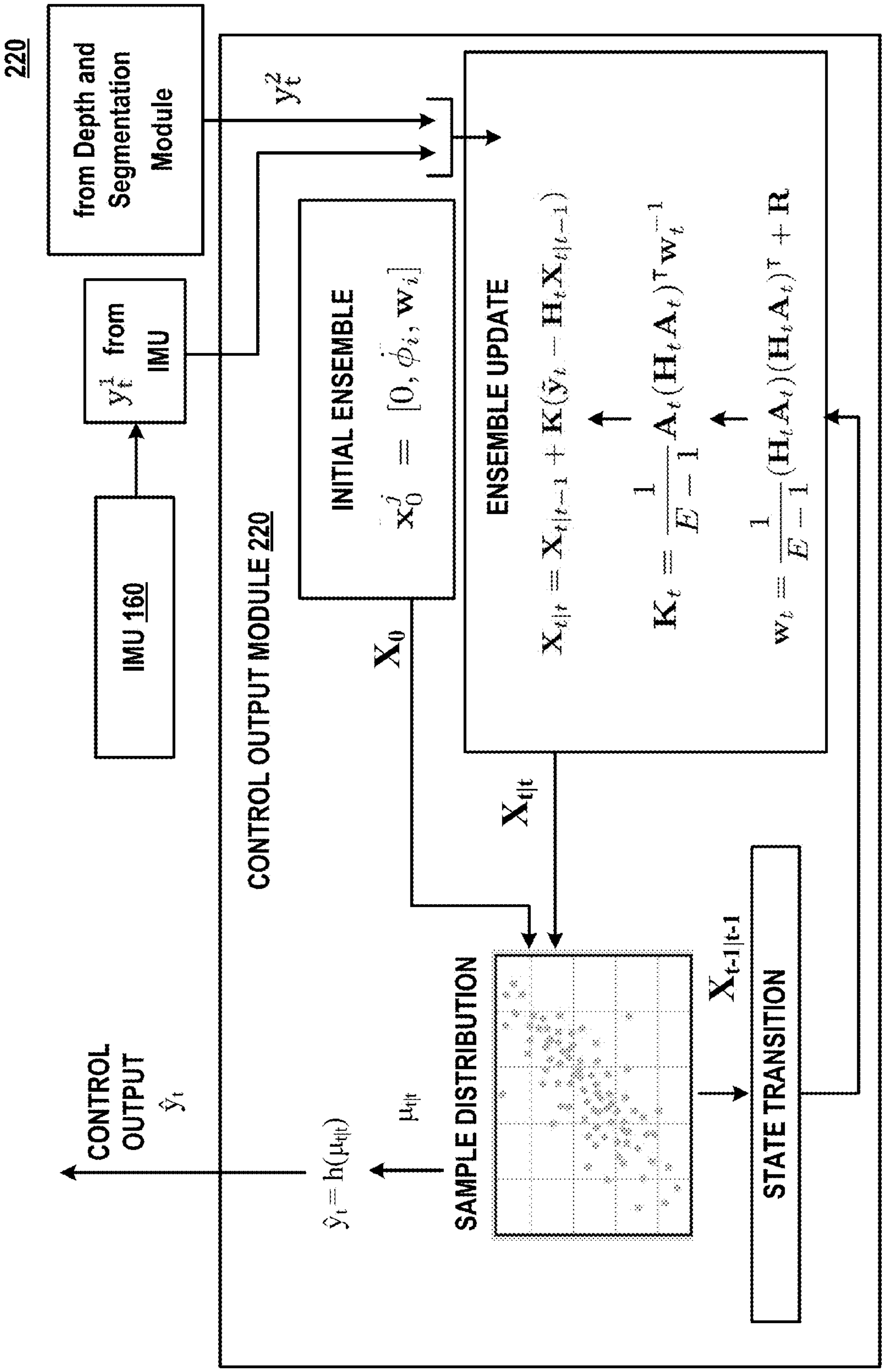
FIG. 2D is a simplified diagram showing an ensemble Bayesian interaction primitive generation model for the framework of FIG. 2A.

Referring to FIG. 2D, the control output module 220 uses ensemble Bayesian interaction primitives (enBIP) to generate environmentally-adaptive control outputs via inference within a latent space based on the extracted depth features from the depth and segmentation module 210. As detailed below, enBIP is an extension of interaction primitives which have been utilized extensively for physical human-robot interaction (HRI) tasks including games of catch, handshakes with complex artificial muscle based humanoid robots, and optimal prosthesis control. A critical feature of enBIPs is their ability to develop learned models of that describe coupled spatial and temporal relationships between human and robot partners, paired with powerful nonlinear filtering, which is why enBIPs work well in human-robot collaboration tasks. The combination of both these neural network modules as well as the learned enBIP model of the framework 200 can be implemented within the system 100 using off-the-shelf components such as a mobile Jetson Xavier board evaluated below.

Depth Prediction Network

Referring to FIGS. 2A-2C and 3, the depth estimation network 212 for depth prediction as implemented by the depth and segmentation module 210 for navigating terrain features is described herein. The depth estimation network 212 uses a combination of convolutional and residual blocks in an autoencoder architecture (AE) to generate depth predictions from RGB image data captured by the camera 110.

Figure 3:
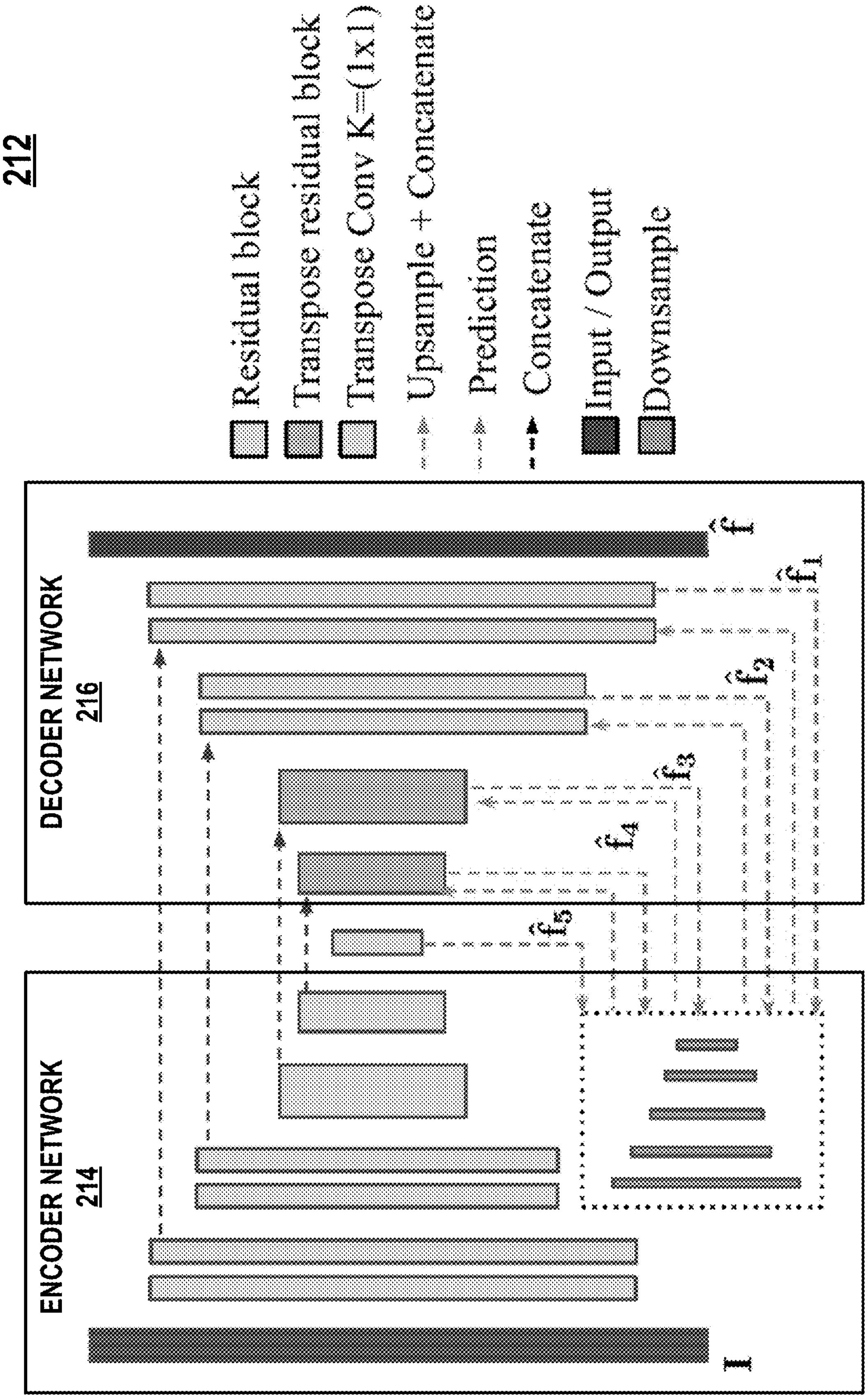
FIG. 3 is a simplified diagram showing a depth prediction neural network for the framework of FIG. 2A.
Figure 4A:
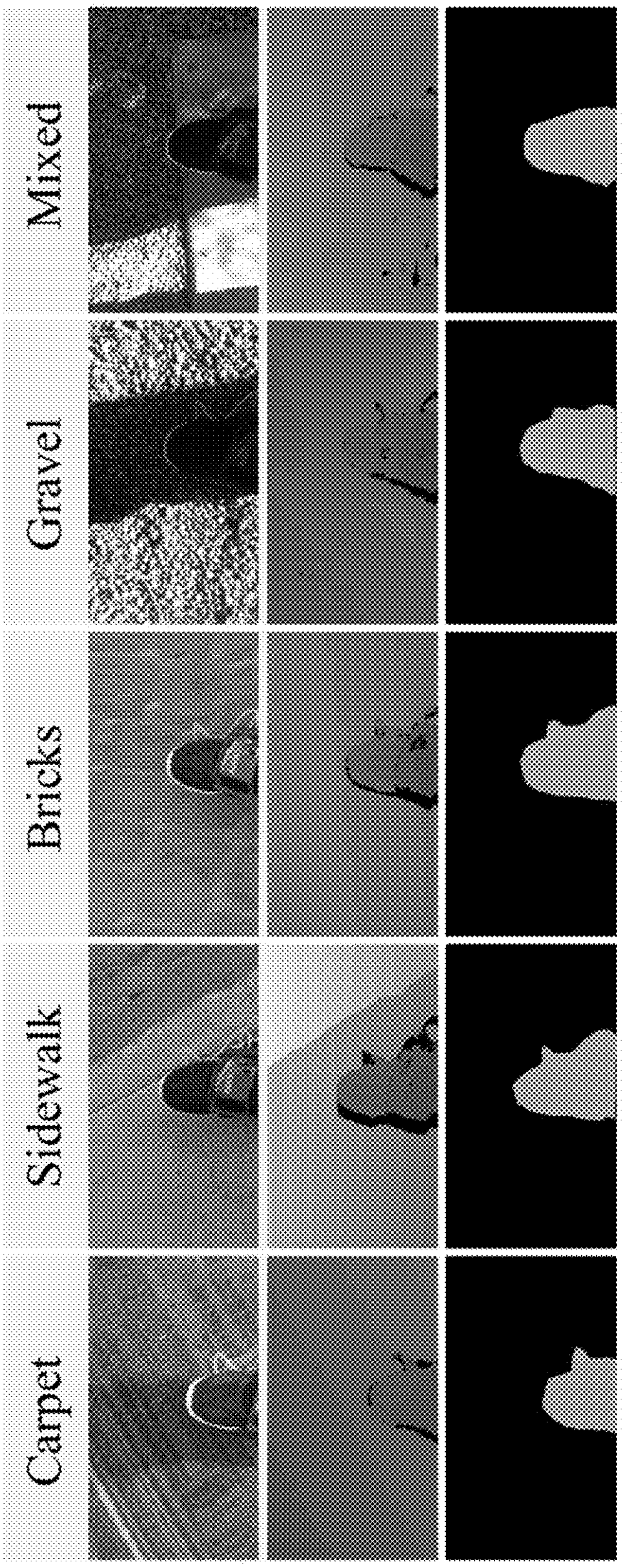
FIGS. 4A and 4B show a series of images showing human walking on different ground surfaces.
Figure 4B:
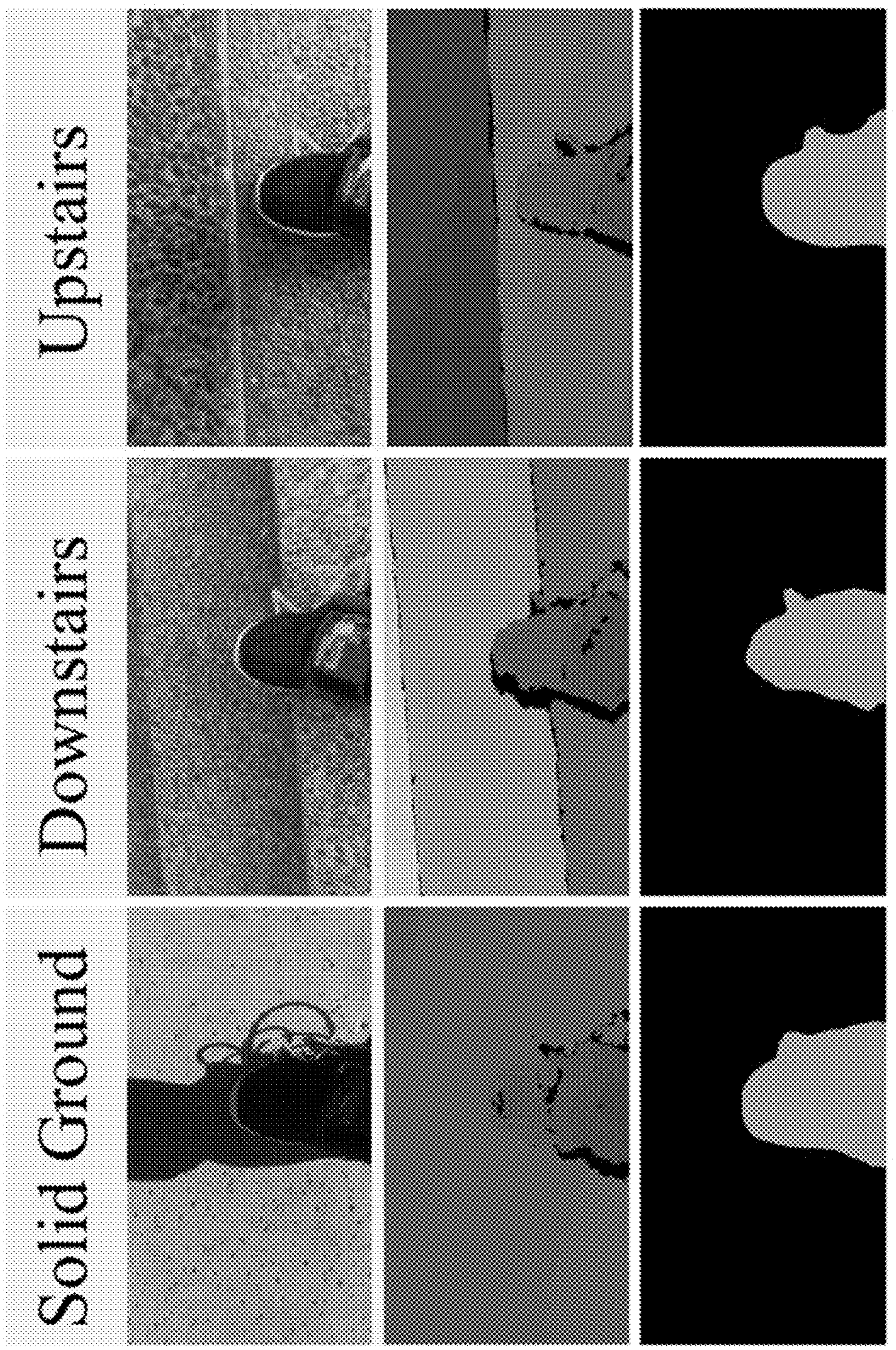

Network Architecture: The depth estimation network 212, shown in FIG. 3, is an AE network which utilizes residual learning, convolutional blocks, and skip connections to ultimately extract a final depth feature estimate f that describe depth features within an image $I_t$ captured by the camera 110. The depth estimation network 212 starts with a encoder network 214 (in particular, a ResNet-50 encoder network, which was shown to be a fast and accurate encoder model) and includes a decoder network 216. Layers of the encoder network 214 and the decoder network 216 are connected via skip connection in a symmetrical manner to provide additional information at decoding time. Finally, the depth estimation network 212 uses a DispNet training structure to implement a loss weight schedule through downsampling. This approach enables the depth estimation network 212 to first learn a coarse representation of depth features from digital RGB images to constrain intermediate features during training, while finer resolutions impact the overall accuracy.

The depth feature extraction process starts with an input image $I_t$ captured by the camera 110, where $I \in \mathbb{R}^{H \times W \times 3}$ and where the image $I_t$ includes RGB data for each pixel therewithin. The input image $I_t$ is provided to the depth estimation network 212. The encoder network 214 of the depth estimation network 212 receives the input image $I_t$ first. As shown, in one embodiment, the encoder network 214 includes five stages. Following a typical AE network architecture, each stage of the encoder network 214 narrows the size of the representation from 2048 neurons down to 64 neurons at a final convolutional bottleneck layer.

The decoder network 216 increases the network size at each layer after the final convolutional bottleneck layer of the encoder network 214 in a pattern symmetrical with that of the encoder network 214. While the first two stages of the decoder network 216 are transpose residual blocks of 3×3 size kernels, the third and fourth stages of the decoder network 216 are convolutional projection layers with two 1×1 kernels each. Although ReLU activation functions connect each stage of the decoder network 216, additional sigmoid activation function outputs facilitate disparity estimation in the decoder network 216 by computing the loss for each output of varied resolutions. The output of the depth estimation network 212 is a combination of a final depth feature estimate $\hat{f} \in \mathbb{R}^{H \times W}$ for the input image $I_t$, as well as intermediate feature map outputs $\hat{f}_n \in \mathbb{R}^{HR_n \times WR_n}$ with $n \leq 5$ for each stage of the decoder network 216 starting at the final convolutional bottleneck layer of the encoder network and $R=[r^{-5}, r^{-4}, r^{-3}, r^{-2}, r^{-1}]$ being a resolution modifier defined by a resolution coefficient r. In one implementation shown in FIG. 3, the decoder network of the depth estimation network 212 provides 1 output and 5 hidden feature map predictions in different resolutions, including estimated depth values for each pixel within the input image $I_t$, with the combination of all outputs denoted as $\hat{D}$ where $\hat{D}=[\hat{f}_5, \hat{f}_4, \hat{f}_3, \hat{f}_2, \hat{f}_1\ \hat{f}]$.

Loss Function: In order to use the full combination of final and intermediate outputs of D in a loss function of the depth estimation network 212 during training, it is necessary to first define a loss £ as a summation of a depth image reconstruction loss ER over each of the prediction of various resolutions (e.g., the final feature map output from a final output layer of the decoder network 216 in addition to intermediate feature map outputs). The loss £ can be described as:

$$\mathcal{L} = \sum_{i=1}^{6} \mathcal{L}_R(D_i \hat{D}_i) w'_i, \tag{1}$$

where estimated depth values at each stage D of the decoder network 216 are compared to a ground truth vector D, downsampled for each corresponding feature map resolution using average pooling operations. The depth estimation network 212 uses a loss weight vector to adjust for each feature size with associated elements of w'=[1/64, 1/32, 1/16, 1/8, 1/4, 1/2]. The depth estimation network 212 uses a reconstruction loss $\mathcal{L}_R$ for depth image reconstruction that includes four loss elements, including: (1) a mean squared error measure $\mathcal{L}_m$, (2) a structural similarity measure $\mathcal{L}_s$, (3) an inter-image gradient measure $\mathcal{L}_g$, and (4) a total variation measure $\mathcal{L}_{tv}$:

$$(d, \hat{d}) = \alpha_1 \mathcal{L}_m + \alpha_2 \mathcal{L}_s + \alpha_3 \mathcal{L}_g + \alpha_4 \mathcal{L}_{tv} \tag{2}$$

where $\hat{d}$ is an iterated depth feature output $\hat{d} \in \hat{D}$ and d is a ground truth feature $d \in D$, and hyperparameters $\alpha_1=102$, $\alpha_2=1$, $\alpha_3=1$, and $\alpha_4=10^{-7}$, influence the importance of each respective loss element on $\mathcal{L}_R$. The mean squared error measure can be represented as:

$$\mathcal{L}_m(d, \hat{d}) = \|d - \hat{d}\|_2^2 \tag{3}$$

A structural similarity index measure (SSIM) is adopted since it can be used to avoid distortions by capturing a covariance alongside an average of a ground truth feature map and a predicted depth feature map. A SSIM loss $\mathcal{L}_s$ can be represented as:

$$\mathcal{L}_s(d, \hat{d}) = \frac{1 - SSIM(d, \hat{d})}{2}. \tag{4}$$

Losses based on inter-image gradient primarily ensure illumination-invariance such that bright lights or shadows cast across the image do not affect the end depth prediction. The inter-image gradient measure $\mathcal{L}_g$ can be implemented as:

$$\mathcal{L}_g(d, \hat{d}) = \frac{1}{n} \sum_{i=1}^{n} (\|\nabla_x d_i - \nabla_x \hat{d}_i\| + \|\nabla_x d_i - \nabla_y \hat{d}_i\|, \tag{5}$$

where $\nabla$ denotes a gradient calculation, and $\|\cdot\|$ is the absolute value. Since $\mathcal{L}_g$ is computed pixelwise both horizontally and vertically, a number of pixels of the output image is denoted as n. In order to add an additional loss to facilitate image deblurring and denoising, the total variation measure $\mathcal{L}_{tv}$ passes the gradient strictly over the output depth feature maps to minimize noise and round terrain features:

$$\mathcal{L}_{tv}(\hat{d}) = \|\nabla_x \hat{d}\|_1 + \|\nabla_y \hat{d}\|_1. \tag{6}$$

Temporal Consistency: Prediction consistency over time is a critical necessity for stable and accurate control of a robotic prosthesis. Temporal consistency of the depth predictions provided by framework 200 is achieved during training via the four loss functions, $\mathcal{L}^m$, $\mathcal{L}_s$, $\mathcal{L}_g$, and $\mathcal{L}_{tv}$ by fine-tuning the depth estimation network 212. In particular, the framework 200 fine-tunes the depth estimation network 212 through application of a temporal consistency training methodology to the resultant depth feature output $\hat{d} \in \hat{D}$, which includes employing binary masks to outline one or more regions within an image which require higher accuracy, and further includes applying a disparity loss $\mathcal{L}_{dis}$ between two consecutive frames including a first frame taken at time t−1 and a second frame taken at time t (e.g., images within video data captured by camera 110). An overlapping mask of the two frames can be defined as M and can be set to equal to the size of a ground truth feature d. As such, the disparity loss $\mathcal{L}_{dis}$ is formulated as:

$$\mathcal{L}_{dis}(\hat{d}_{t=1}, \hat{d}_t) = \beta_1 \mathcal{L}_m(\hat{d}_{t-1}^M, \hat{d}_t^M) + \beta_2 \mathcal{L}_s(\hat{d}_{t-1}^M, \hat{d}_t^M) + \gamma(\mathcal{L}_R(d_{t-1}, \hat{d}_{t-1}) + \mathcal{L}_R(d_t, \hat{d}_t)). \tag{7}$$

where $$\hat{d}_t^M$$

indicates for a predicted frame at time t with a binary mask applied:

$$\hat{d}_t^M = \hat{d}_t \cdot M.$$

Additionally, to sustain the precision of prediction over time, the framework 200 applies $\mathcal{L}_R$ is on each frame individually. Each loss element of the fine-tuning process is weighted by corresponding hyperparameters, $\beta_1=0.7$, $\beta_2=0.3$, $\gamma-10$. The fine-tuning step, therefore, makes the predicted frames more similar to one another in static regions while maintaining the reconstruction accuracy from prior network training.

Control Outputs Using Ensemble Bayesian Interaction Primitives

Given the extracted environmental information provided by depth and segmentation module 210 including depth features $\hat{D}=[\hat{f}_5, \hat{f}_4, \hat{f}_3, \hat{f}_2, \hat{f}_1\ \hat{f}]$. for each pixel within images captured by the camera 110, the control output module 220 uses enBIP to generate appropriate responses for the prosthetic or orthotic joint 130. As a data-driven method, enBIP uses example demonstrations of interactions between multiple agents to generate a behavior model that represents an observed system of human kinematics with respect to the prosthetic or orthotic joint 130. enBIP was selected as a modeling formulation for this purpose because enBIP enables inference of future observable human-robot states as well as non-observable human-robot states. Additionally, enBIP supplies uncertainty estimates which can allow a controller such as computing device 120 to validate predicted control actions, possibly adding modifications if the model is highly unsure. Lastly, enBIP provides robustness against sensor noise as well as real-time inference capabilities in complex human-robot interactive control tasks.

In one aspect, assisted locomotion with a prosthetic or orthotic is cast as a close interaction between the human kinematics, environmental features, and robotic prosthetic. The control output module 220 incorporates environmental information in the form of predicted depth features along with sensed kinematic information from an inertial measurement unit (IMU) 160 (FIGS. 2A and 2B) and prosthesis control signals into a single holistic locomotion model. The control output module 220 uses kinematic sensor values, along with processed depth features and prosthesis control signals from n E N observed behavior demonstrations (e.g., demonstrated strides using the prosthetic or orthotic joint 130), to form an observation vector $[y_1, \ldots y_{Tn}], \in \mathbb{R}^{D_y \times T_n}$ for $D_y$ variables in $T_n$ time steps. As such, by capturing the observed behavior demonstrations of the prosthetic or orthotic joint 130, the control output module 220 can incorporate human kinematic properties and environmental features within the latent space to generate appropriate control signals that take into account human kinematic behavior especially in terms of observable environmental features (which can be captured at the depth and segmentation module 210).

Latent Space Formulation: Generating an accurate model from an example demonstration matrix would be difficult due to high internal dimensionality, especially with no guarantee of temporal consistency between demonstrations. One main goal of a latent space formulation determined by control output module 220 is therefore to reduce modeling dimensionality by projecting training demonstrations (e.g., recorded demonstrations of human-prosthesis behavior) into a latent space that encompasses both spatial and temporal features. Notably, this process must be done in a way that allows for estimation of future state distributions for both observed and unobserved variables $Y_{t+1:T}$ with only a partial observation of the state space and the example demonstration matrix $$Y\frac{1}{1:T_1}, \ldots, Y\frac{N}{1:T_N}:$$

$$p\left(\hat{Y}_{t+1:T} \mid y_{1:t}, Y^1_{1:T_1}, \ldots, Y^N_{1:T_N}\right). \tag{8}$$

Basis function decomposition sidesteps the significant modeling challenges of requiring a generative model over all variables and a nonlinear transition function. Basis function decomposition enables the control output module 220 to approximate each trajectory as a linear combination of $B^d$ functions in the form of:

$$Y_t^d = \Phi_{\phi(t)}^T w^d + \in_y.$$

Each basis function $\Phi_{\phi(t)} \in \mathbb{R}^{B^d}$ is modified with corresponding weight parameters $w^d \in \mathbb{R}^{B^d}$ to minimize an approximation error $\in_y$. As a time-invariant dimensionality reduction method, the control output module 220 includes a temporal shift to the relative time measure phase $\phi(t) \in \mathbb{R}$, where $0 \leq \phi(t) \leq 1$.

Although the time-invariant latent space formulation facilitates estimation of entire trajectories, filtering over both spatial and temporal features interactions was more robust and accurate. As such, the control output module 220 incorporates phase, phase velocity, and weight vectors, $w=[\phi, \dot{\phi}, w^{0T}, \ldots, w^{DT}] \in \mathbb{R}^B$ where $$B = \sum_d^D B^d$$

into the state representation. By assuming that a training demonstration advances linearly in time, the phase velocity is estimated with, $$\phi = \frac{1}{T_n}.$$

Substituting the weight vector into 8 and applying the Bayes' rule yields:

$$p(w_t Y_{1:t}, w_0) \propto p(y_t \mid w_t) p(w_t Y_{1:t}, w_0) \tag{9}$$

since the time-invariant weight vector $p(w_t Y_{1:t}, w_0)$, models the entire trajectory Y.

Inference: In order to accommodate a variety of control modifications based on observed or predicted environmental features, the control output module 220 leverages ensemble Bayesian estimation from enBIP to produce approximate inferences of the posterior distribution according to Equation (9), which include human kinematics and environmental features. Assuming, of course, that higher-order statistical moments between states are negligible and that the Markov property holds. Algorithmically, enBIP first generates an ensemble of latent observation models, taken randomly from the demonstration set. As the subject walks with the prosthetic or orthotic joint 130, the control output module 220 propagates the ensemble forward one step with a state transition function. Then, as new sensor and depth observations periodically become available as the camera 110 and the depth and segmentation module 210 work, the control output module 220 performs a measurement update step across the entire ensemble. From the updated ensemble, the control output module 220 calculates the mean and variance of each latent component, and subsequently projects the mean and variance into a trajectory space by applying the linear combination of basis functions to the weight vectors.

The control output module 220 uniformly samples the initial ensemble of E members $X=[x^1, \ldots, x^E]$ from the observed demonstrations $$x_0^j = [0, \phi_i, w_i], 1 \le j \le E$$

with $i \sim \mathcal{U}(1,N)$, and $E \le N$. Inference through Bayesian estimation begins as the control output module 220 iteratively propagates each ensemble member forward one step to approximate $p(w_t|y_{t-1}, w_0)$ with:

$$x_{t|t-1}^j = g(x_{t-1|t-1}^j) + \epsilon_x, 1 \le j \le E, \tag{10}$$

which utilizes a constant-velocity state transition function $g(\cdot)$ and stochastic error $\epsilon_x \approx N(0, Q_t)$, estimated with a normal distribution from the sample demonstrations. Next, the control output module 220 updates each ensemble member with the observation through the nonlinear observation operator $h(\cdot)$, $$H_t X_{t|t-1} = \left[h(x_{t|t-1}^1), \ldots, h(x_{t|t-1}^E)\right]^T. \tag{11}$$

followed by computing a deviation of the ensemble from the sample mean:

$$H_t A_t = H_t X_{t|t-1} - \left[\frac{1}{E}\sum_{j-1}^{E} h(x_{t|t-1}^j), \ldots, \frac{1}{E}\sum_{j=1}^{E} h(x_{t|t-1}^j)\right]. \tag{12}$$

The control output module 220 uses the deviation $H_tA_t$ and observation noise R to compute an innovation covariance:

$$w_t = \frac{1}{E-1}(H_t A_t)(H_t A_t)^T + R. \tag{13}$$

The control output module 220 uses the innovation covariance as well as the deviation of the ensemble to calculate the Kalman gain from the ensemble members without a covariance matrix through:

$$A_t = X_{t|t-1} - \frac{1}{E}\sum_{j=1}^{E} x_{t|t-1}^t, \tag{14}$$

$$K_t = \frac{1}{E-1} A_t (H_t A_t)^T w_t^{-1}. \tag{15}$$

Finally, the control output module 220 realizes a measurement update by applying a difference between a new observation at time t and an expected observation given t−1 to the ensemble through the Kalman gain, $$\tilde{y}_t = \left[y_t + \epsilon_y^1, \ldots, y_t + \epsilon_y^E\right], \tag{16}$$

$$X_{t|t} = X_{t|t-1} + K(\tilde{y}_t - H_t X_{t|t-1}). \tag{17}$$

The control output module 220 accommodates for partial observations by artificially inflating the observation noise for non-observable variables such as the control signals such that the Kalman filter does not condition on these unknown input values.

Experiments and Results

To validate the system 100, a number of experiments were conducted with a focus on real-world human-subject data. The following describes in detail how the data was collected, processed, and how the models were trained, including specific hardware and software utilized. To better discuss specific model results, the following experimental section is further broken up into experiments and results for (1) the network architecture and (2) the enBIP model with environmental awareness. Experiment 1 examines the efficacy of our network architecture in predicting accurate depth values from RGB images collected from a body mounted camera. While Experiment 2 applies the network architecture on embedded hardware to infer environmentally conditioned control trajectories for a lower-limb prosthesis in a testbed environment.

Data Collection

Multimodal data sets were collected from participants who were outfitted with advanced inertial measurement units (IMUs) and a camera/depth sensor module. The IMUs are BNO080 system-in-package and include a triaxial accelerometer, a triaxial gyroscope, and a magnetometer with a 32-bit ARM Cortex microcontroller running Hillcrest Labs proprietary SH-2 firmware for sensor filtering and fusion. IMU devices are combined with an ESP32 microprocessor, in ergonomic cases that can easily be fitted to subjects' bodies over clothing, to send Bluetooth data packages out at 100 Hz. These inertial sensor modules were mounted to the subjects' lower limb and foot during the data collection process to collect kinematic data. However, during the testing phase, the foot sensor is removed. Additionally, an Intel RealSense D435 depth camera module was mounted to the subjects' lower limb.

A custom vision data set of 57 varied scenes was collected with over 30,000 RGB-depth image pairs from the lower-limb, during locomotion tasks in a dynamic urban environment. Data collection involved a subject walking over various obstacles and surfaces, including, but not limited to: sidewalks, roadways, curbs, gravel, carpeting, and up/down stairs; in differing lighting conditions at a fixed depth range (0.0-1.0 meters). Example images from the custom data set are visible in the upper row of FIGS. 4A and 4B with images of the subject walking in various scenes. The second row of FIGS. 4A and 4B visualizes the depth values of the same image using a color gradient; darker coloring indicates closer pixels while lighter pixels are further away. A custom annotated mask is shown in the third row of FIGS. 4A and 4B. These masks are used to train a masked RCNN model predicting human stepping areas. The semantic masks are also implemented to improve the temporal consistency.

Experiment 1: Neural Network Evaluation

In order for the network architecture of depth estimation network 212 to operate under real-world conditions, it must have both a low depth-prediction error, as well as real-time computation capabilities. The following section details the learning process and accuracy of our network architecture on the custom human-subject data set.

TABLE 1

Comparisons of different decoder architectures on the custom dataset. Result Evaluations and Ablation Study

| Encoder | Decoder | abs REL ↓ | sq REL ↓ | RMSE ↓ | RMSE log ↓ | $\delta_1$↑ | $\delta_2$↑ | $\delta_3$↑ | TC↓ |
|---|---|---|---|---|---|---|---|---|---|
| ResNet-50 | Residual Blocks | 0.2292 | 0.0530 | 0.0841 | 0.0615 | 0.8144 | 0.9140 | 0.9575 | 0.000194 |
| | Conv Blocks + DispNet | 0.2285 | 0.0504 | 0.0808 | 0.0605 | 0.8057 | 0.9423 | 0.9656 | 0.000184 |
| | Residual Blocks + Dispnet | 0.2250 | 0.0494 | 0.0856 | 0.0633 | 0.7860 | 0.9175 | 0.9643 | 0.000195 |
| | System 100 | 0.2205 | 0.0480 | 0.0753 | 0.0567 | 0.8227 | 0.9227 | 0.9658 | 0.000179 |

The last row shows results from the present depth estimation model. 1 indicates the higher the better; \ indicates the lower the better.

Figure 5A:
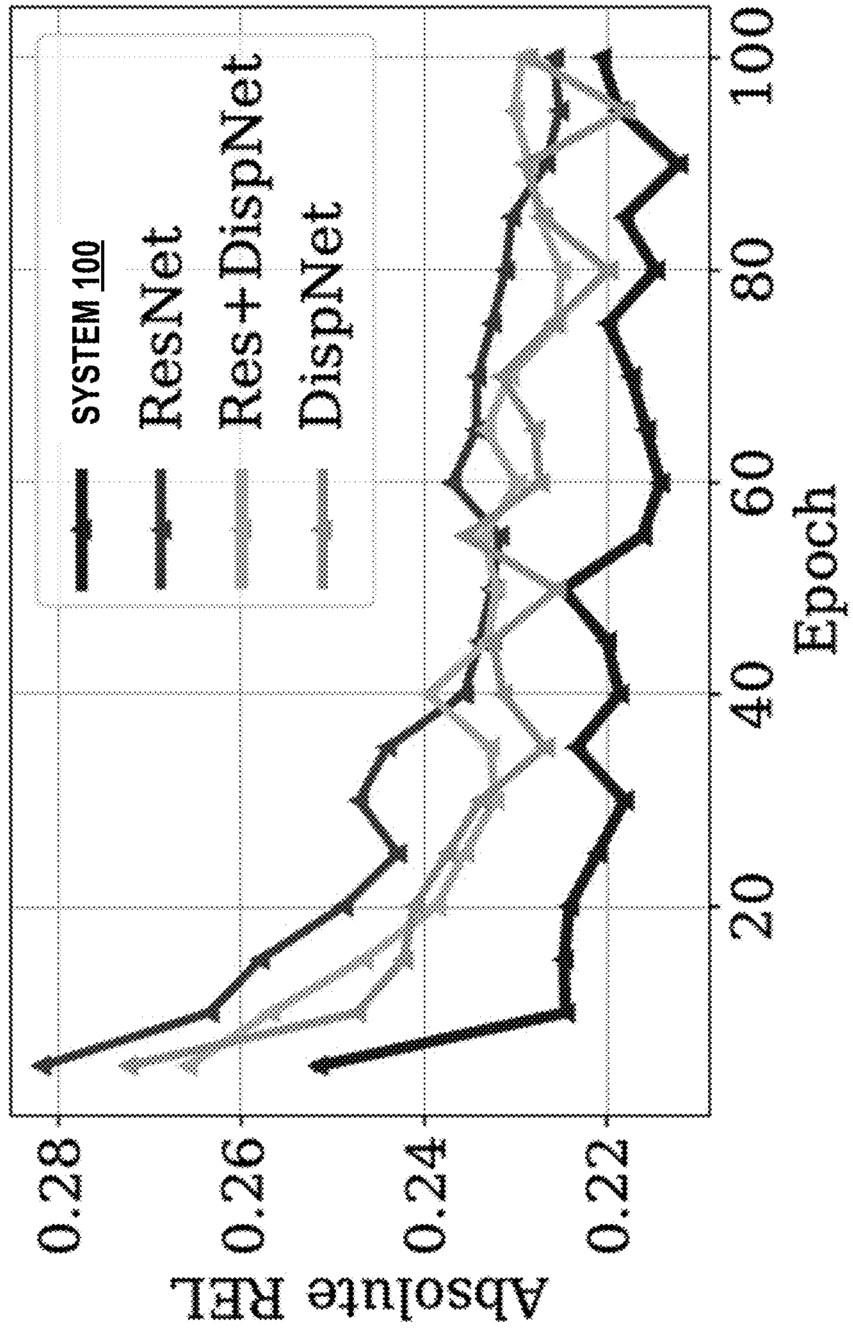
FIGS. 5A and 5B show a series of images showing validation of the framework of FIG. 2A.
Figure 5B:
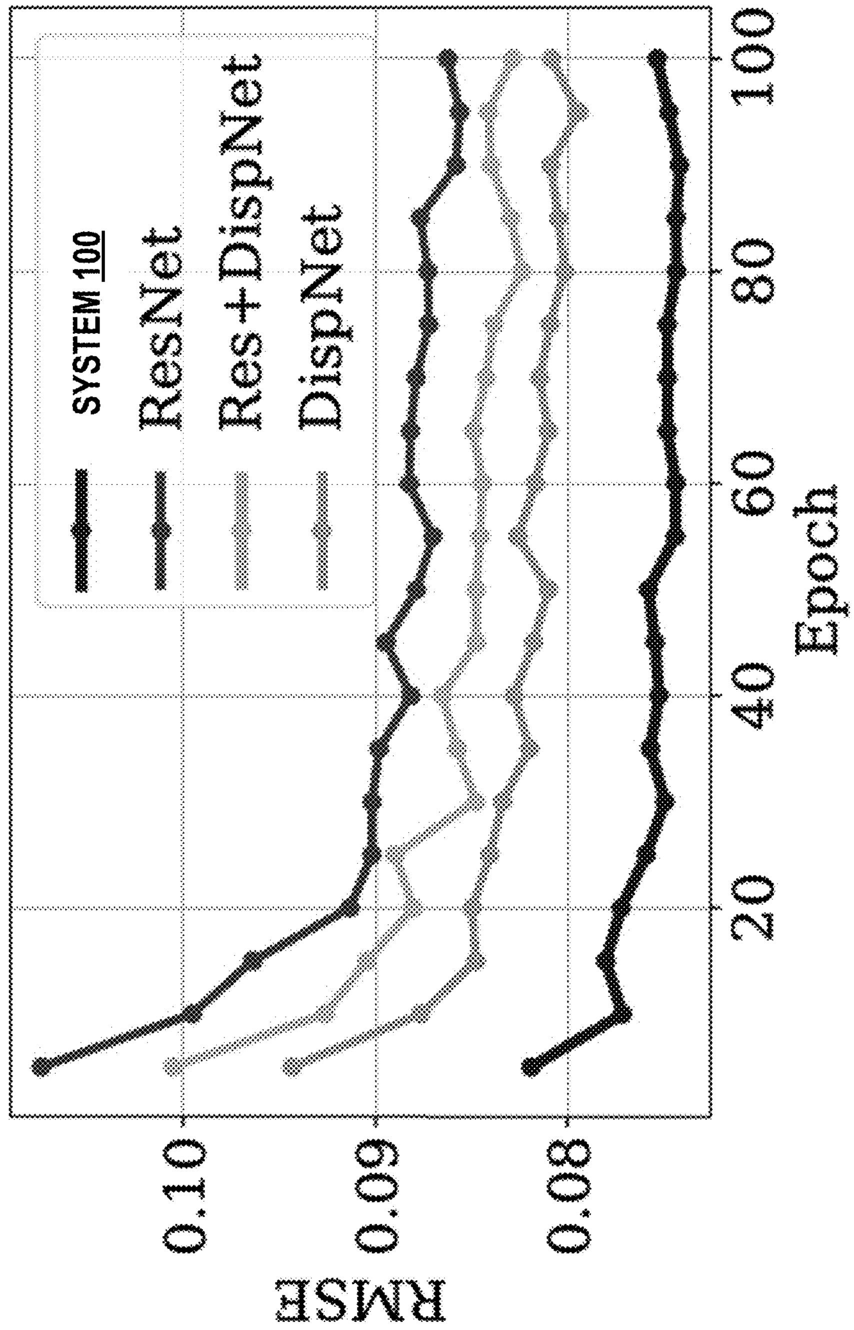

Training: 80% (46 scenes) of the custom data set was utilized for training and 20% (11 scenes) were utilized for testing. Adam was selected as the optimizer with learning rate $n_1=10^{-5}$. The input has the shape 90×160×3, whereas the ground truth and the output have the shape of 90×160×1. The ground truth is down-sampled to 3×5, 6×10, 12×20, 23×40, and 45×80 for the loss weight schedule of DispNet. Training was performed on 3 other AE architectures for comparison in an empirical manner. Residual learning, DispNet, and the combination of using convolutional layers are investigated for the decoder network 216 (see Table. I). All models were trained for 100 epochs and fine-tuned by applying a disparity loss with learning rate $n_2=10^{-7}$ for 30 epochs. FIGS. 5A and 5B show the validation among 4 models using the absolute REL and RMSE metrics.

A pre-trained masked RCNN was used as the masking network for object detection. The masked RCNN was fine-tuned given masks provided from the custom dataset using binary cross-entropy loss.

Figure 6:
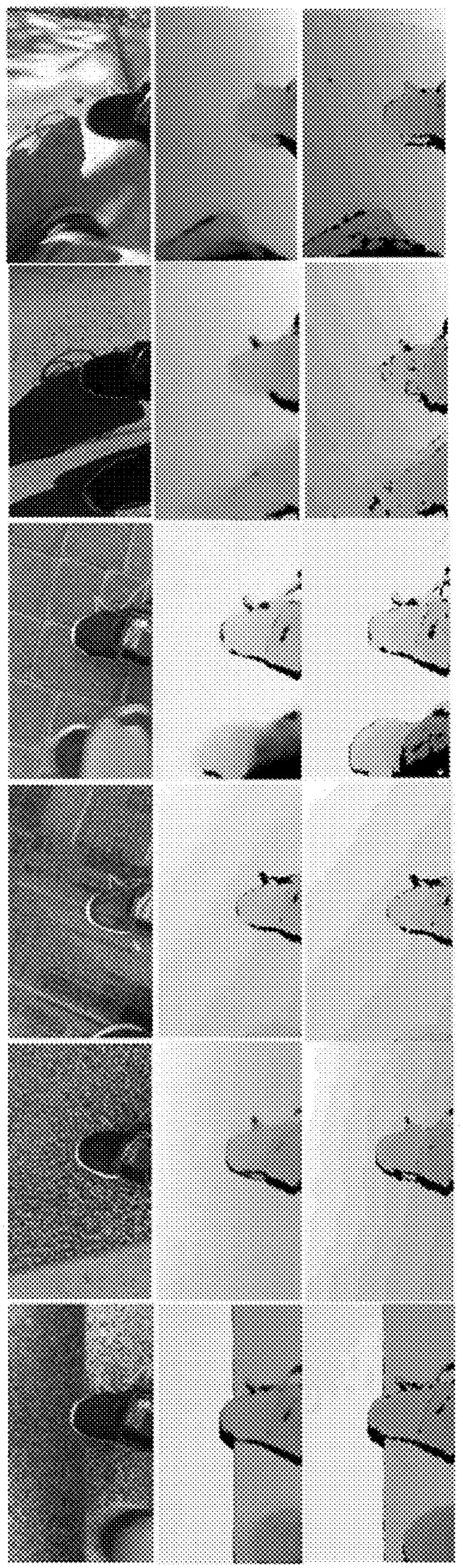
FIG. 6 shows a series of images illustrating a predicted depth map with respect to a ground truth depth map by the framework of FIG. 2A.

Results: The depth prediction results shown in FIG. 6 demonstrate prediction accuracy while walking in different conditions. Comparing the middle row and the bottom row of FIG. 6, it can be seen that the predicted depth images exhibit a smoothing effect with less pixel to pixel noise than the original input. Additionally, sharp features in the environment, such as the stairs or curbs result in a delectably sharper edge between the two surfaces. Finally, the depth prediction network is shown to be accurate over a range of ground materials and patterns, such as solid bricks, concrete, aggregate gravel, carpet, and laminate stairs. The present depth-prediction network achieves depth estimation regardless of the ground material, lighting, or environmental features. It is particularly important to note that shadows (which are typically induced by the user) do not negatively affect the depth prediction performance.

Evaluation: The evaluation and the ablation study of the depth prediction results are shown in Table I, the evaluation process takes the RGB data from testing set and compared the model predictions with the ground truth in terms of commonly accepted evaluation metrics-absolute REL, sq REL, RMSE, RMSE log, $\delta_1$, $\delta_2$ and $\delta_3$, where $\delta_N$, is the percentage of the ground truth pixels under the constraint:

$$\max\left(\frac{\hat{d}_i}{d_i}, \frac{d_i}{\hat{d}_i}\right) < 1.25^N$$

since the for temporal consistency, $\mathcal{T}$C is proposed as the metric for consistency evaluation:

$$\mathcal{TC} = \frac{1}{T-1}\sum_{t=2}^{T}\left(\frac{1}{\Sigma_{i=1}^{n} M_i}\left\|\hat{d}_{t-1}^{M} - \hat{d}_t^{M}\right\|_2\right), \tag{18}$$

where T is the number of frames in a video sequence. Since the terrain from the camera view is dynamic, we conclude the lower $\mathcal{T}$C the better under the constrain:

$$\mathcal{TC} \gtrapprox 0.$$

Figure 8B:
FIGS. 8A and 8B show a series of images illustrating depth estimation with point cloud view.
Figure 8A:
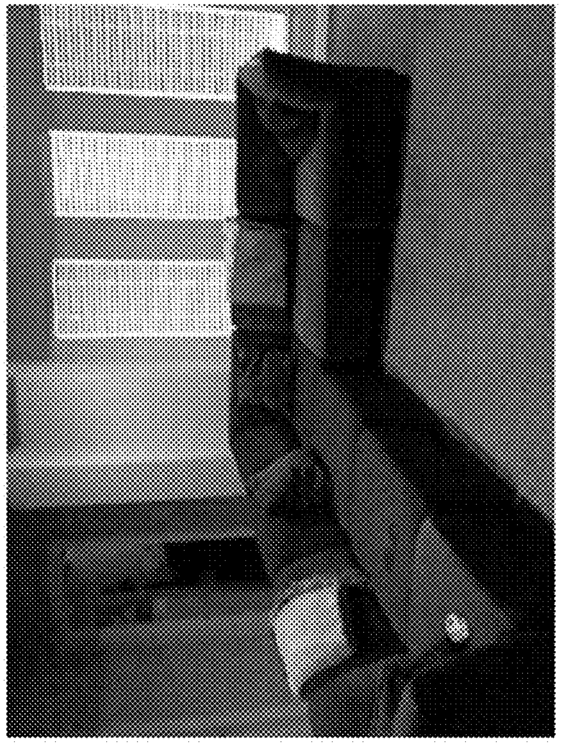
Figure 9:
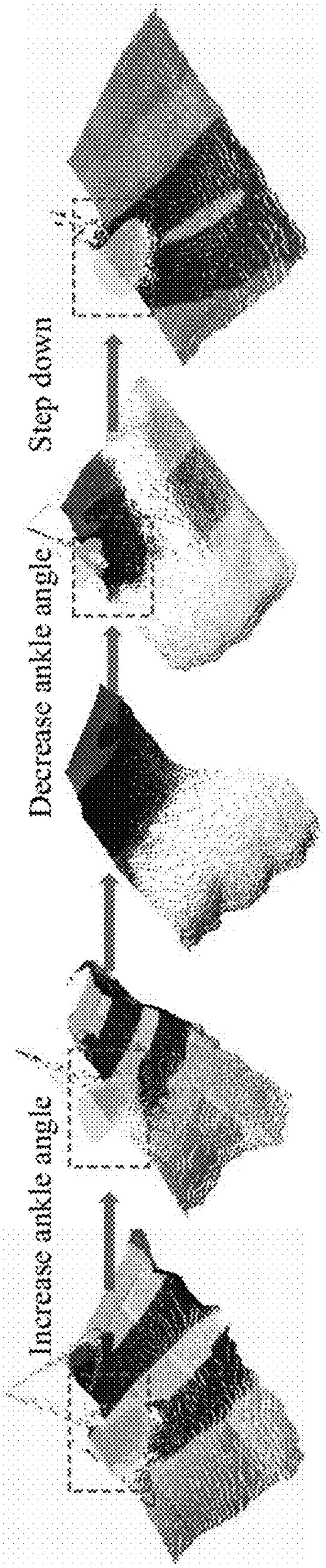
FIG. 9 is an image showing a 3D point cloud for depth estimation of a subject stepping on a stair.

Another visual way in evaluating depth estimation models is to review 3D point clouds generated with predicted depth maps. FIG. 8B shows one sample point cloud for an image (FIG. 8A) of the NYU-v2 data set (on which the system 100 did not train). In a similar vein, FIG. 9 depicts point clouds generated during an example task of stepping on a stair.

Because the final version of the framework 200 must integrate with the prosthetic or orthotic joint 130 and it must be capable of fast inference over a range of environmental variables. Therefore, the framework 200 was deployed on an embedded hardware serving as the computing device 120, which is in some embodiments a Jetson Xavier NX, which is a system on module (SOM) device capable of up to 21 TOPS of accelerated computing and tailored toward streaming data from multiple sensors into modern deep neural networks. The framework 200 performed inference in an average of 0.0860 sec (11.57 FPS) with a standard deviation of 0.0013 sec.

Experiment 2: Prosthesis Evaluation

One critical use of environmental and terrain awareness is in stepping over curbs or onto stairs. If a terrain prediction algorithm is even 99% effective in stair prediction it would still pose a grave safety concern, due to the chances of causing the subject to fall down a set of stairs. Since environmental features are directly incorporated with a very high accuracy, the evaluation focuses experimentally on two criteria in the prosthesis experiments (1) "Can enBIP model stair stepping over a range of step distances?" and (2) "For a given step, does incorporating environmental features produce a more accurate model?".

Training: Collected data for stair stepping was used to train an enBIP model with modalities from tibia-mounted inertial sensors, predicted depth features, and the ankle angle control trajectory. To produce depth features from the predicted depth map, the system 100 took the average over two masks which bisect the image horizontally and subtracting the area behind the shoe from the area in front. A one-dimensional depth feature was produced which showed the changes in terrain due to slopes or steps. While the depth features for this experiment were simplified, other and more complex features were possible, such as, calculating curvature, detecting stair edges, or incorporating the entire predicted depth map. Subjects were asked to perform 50 steps of stair-stepping up onto a custom built curb during which the subject was instructed to start from with their toe at varying positions away from the curb in a range from 0 inches to 16 inches. Applying the framework 200, the system 100 ends up with a generic model to predict ankle angle control actions given IMU observations and depth features. The compiled point cloud in FIG. 9 from one example demonstration illustrates the accuracy of the depth prediction method of depth and segmentation module 210 during experimentation.

Figure 10:
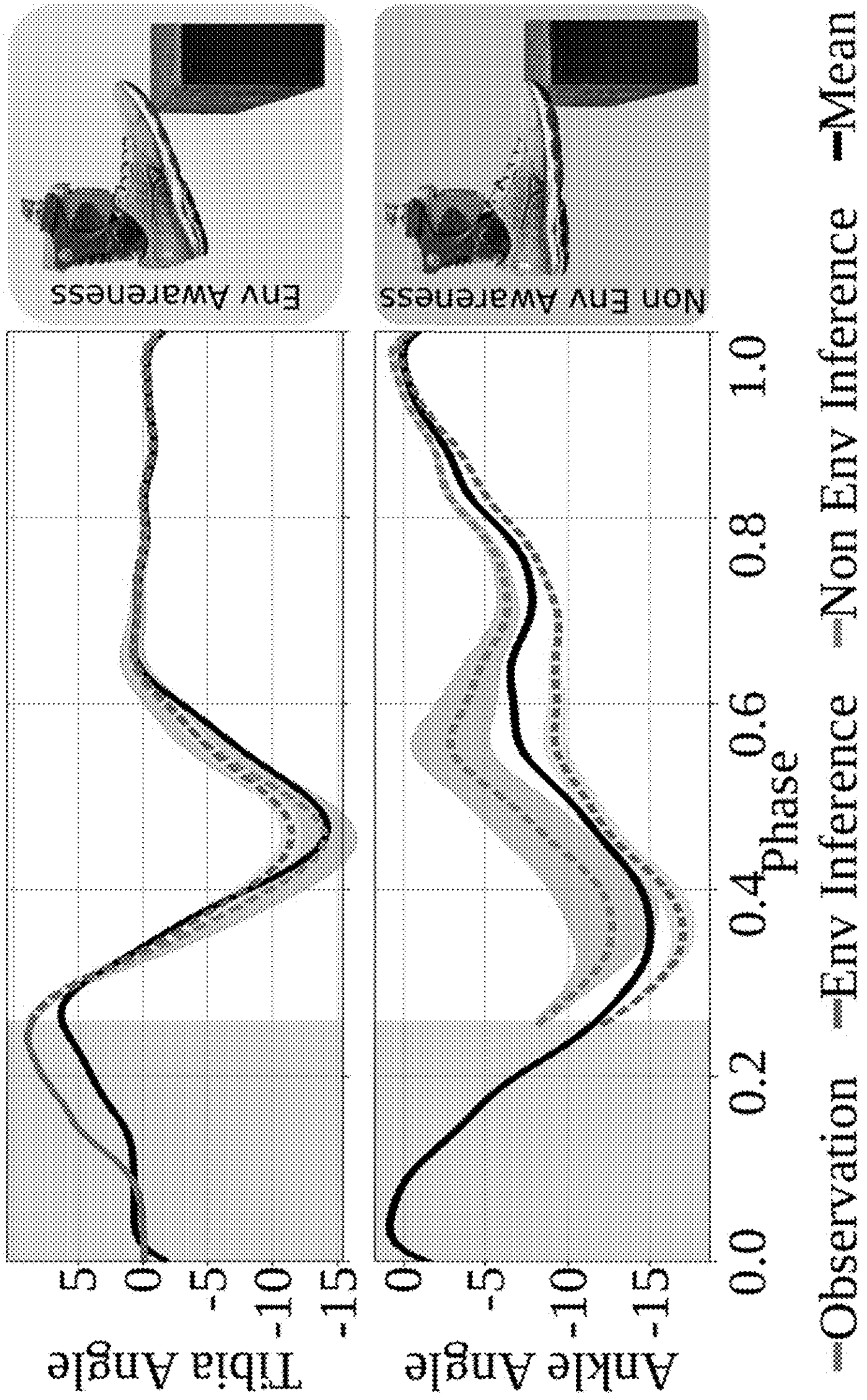
FIG. 10 is a graphical representation showing prediction of an ankle angle control trajectory for a single step.

Results: The system 100 produced an average control error of 1.07° over 10 withheld example demonstration when using depth features for the stair stepping task compared to an average control error of 6.60° without depth features. The system 100 performed even better when examined at 35% phase, the approximate temporal location where the foot traverses the leading edge of the stair, with average control error of 2.32° compared to 9.25° for inference with kinematics only. FIG. 10 highlights the difference between inference with and without environmental awareness, where from the partial observation of a stepping trajectory the system 100 produced two estimates of the control trajectory both with and without environmental awareness. Inference with environmental awareness (blue) has a low variance, which shows high confidence by the model, and withdraws the toe substantially based on the observed depth features. However, without environmental awareness (green) the model does not have adequate information to form an inference with high confidence leading to both an increase in variance, as well as a control trajectory which does not sufficient dorsiflexion to the foot to clear the curb.

Figure 7:
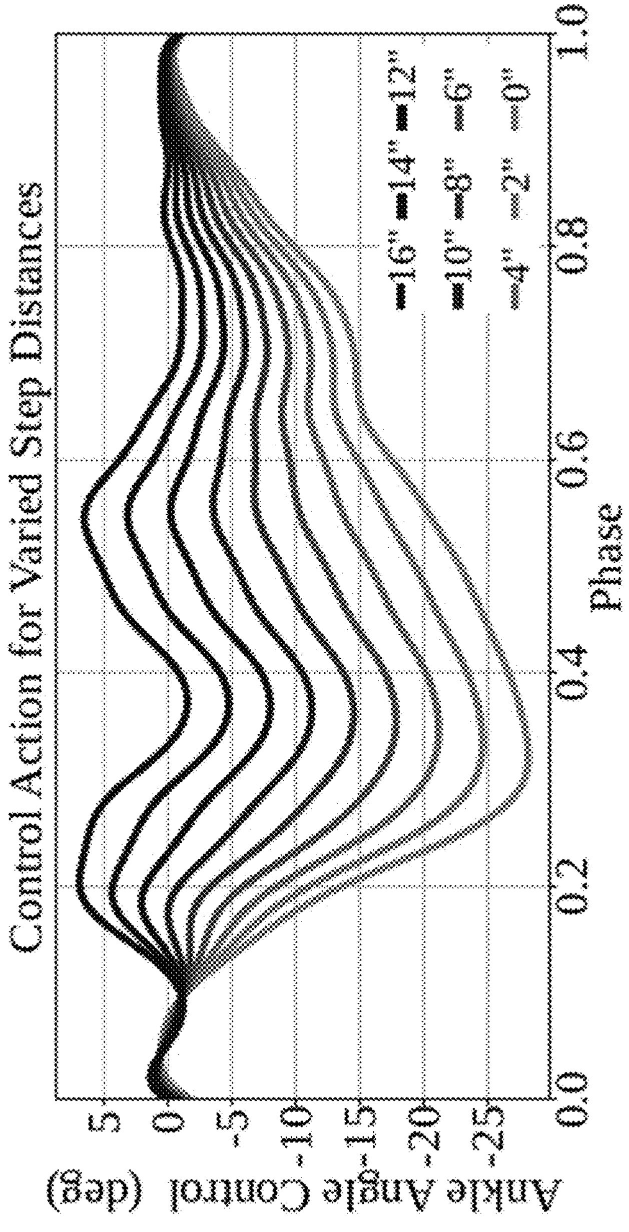
FIG. 7 is a graphical representation showing prediction of the ankle angle control trajectory for an entire phase of walking by the system of FIG. 1.

FIG. 7 shows the range of possible control actions at the start of the stride given the position of the step as seen through the predicted depth features. Given the same initial conditions the horizontal position of the step in reference to the foot clearly modifies the ankle angle control trajectory. When the step is very close, the ankle angle must increase dramatically to pull the toe up such that there is no collision with the edge of the step. Likewise, as the step is moved away from the foot the ankle must first apply plantarflexion to push off the ground before returning to the neutral position before heel-strike.

Methods

FIGS. 11A-11F are a series of process flows showing a method 300 for implementing aspects of the system 100 and associated framework.

Figure 11A:
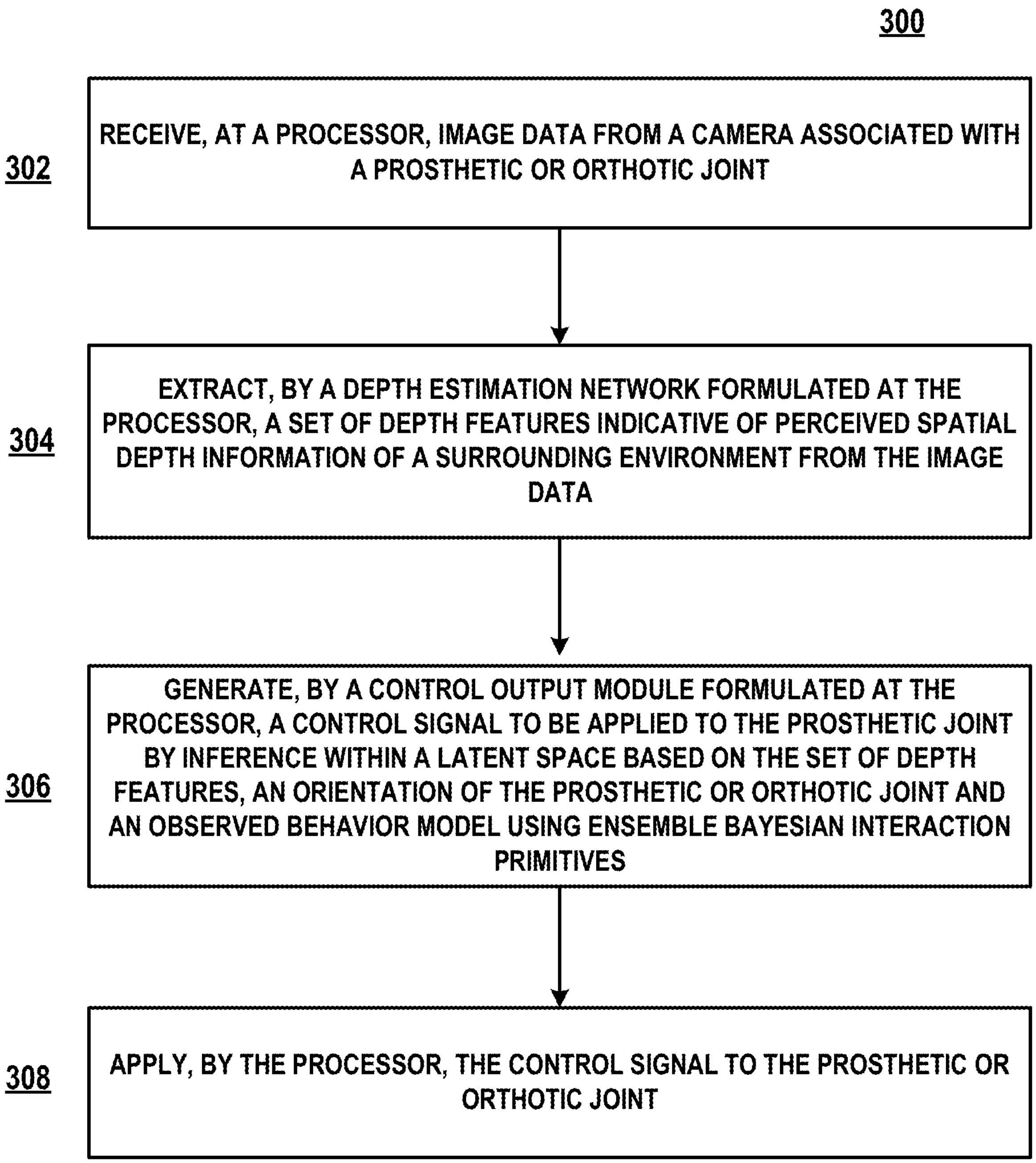
FIGS. 11A-11F are a series of process flows showing a method that implements aspects of the framework of FIGS. 2A-2D.

At block 302 of method 300 shown in FIG. 11A, a processor receives image data from a camera associated with a prosthetic or orthotic joint. At block 304, the processor extracts, by a depth estimation network formulated at the processor, a set of depth features indicative of perceived spatial depth information of a surrounding environment from the image data. At block 306, the processor generates, by a control output module formulated at the processor, a control signal to be applied to the prosthetic or orthotic joint by inference within a latent space based on the set of depth features, an orientation of the prosthetic or orthotic joint and an observed behavior model using ensemble Bayesian interaction primitives. At block 308, the processor applies the control signal to the prosthetic or orthotic joint.

Figure 11B:
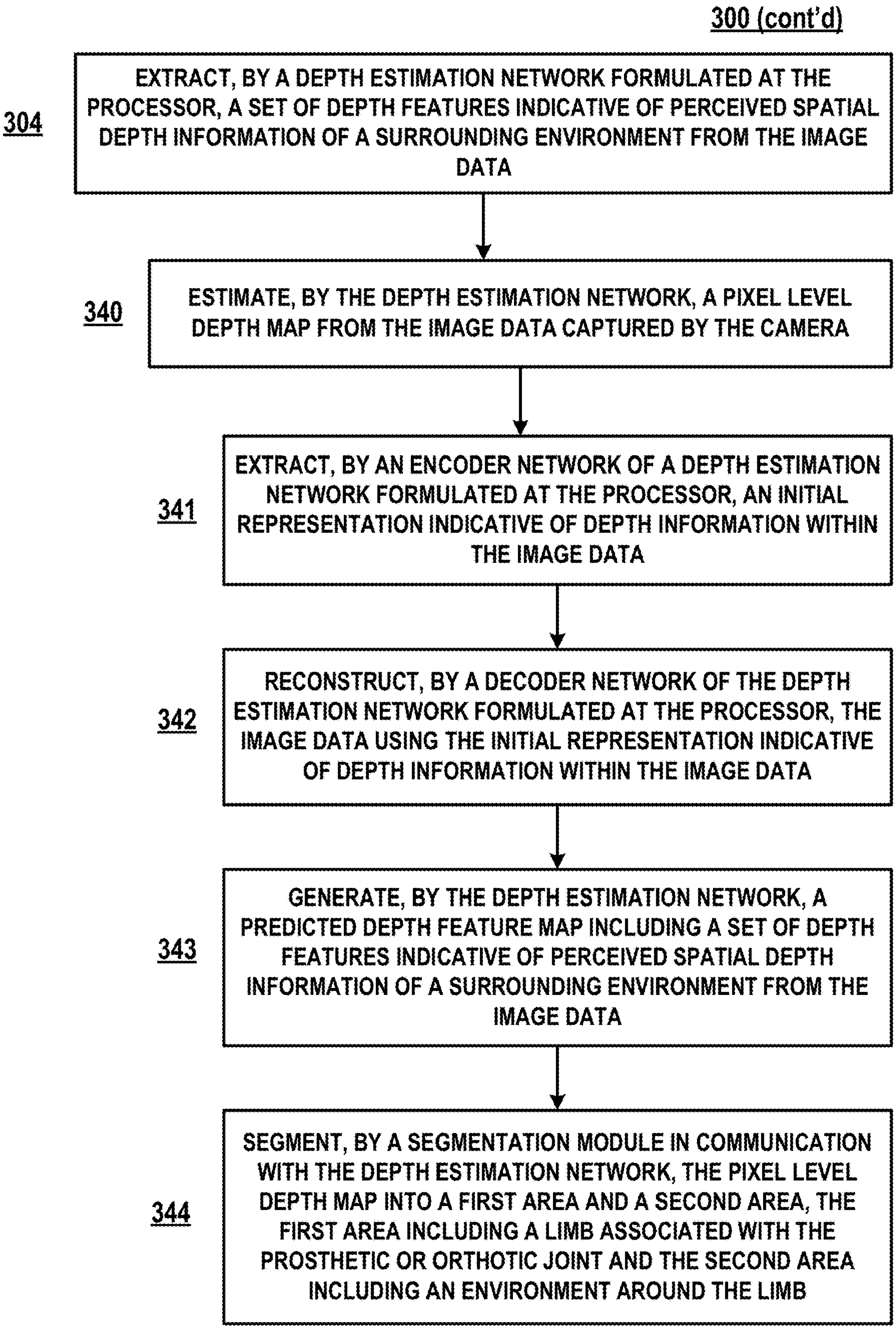

With reference to FIG. 11B, block 304 includes a sub-block 340, at which the processor estimates, by the depth estimation network, a pixel level depth map from the image data captured by the camera. Sub-block 340 includes sub-block 341 in which the processor extracts, by an encoder network of a depth estimation network formulated at the processor, an initial representation indicative of depth information within the image data. At sub-block 342, the processor reconstructs, by a decoder network of the depth estimation network, the image data using the initial representation indicative of depth information within the image data. At sub-block 343, the processor generates, by the depth estimation network, a predicted depth feature map including a set of depth features indicative of perceived spatial depth information of a surrounding environment from the image data. At block 344, the processor segments, by a segmentation module in communication with the depth estimation network, the pixel level depth map into a first area and a second area, the first area including a limb associated with the prosthetic or orthotic joint and the second area including an environment around the limb.

Figure 11C:
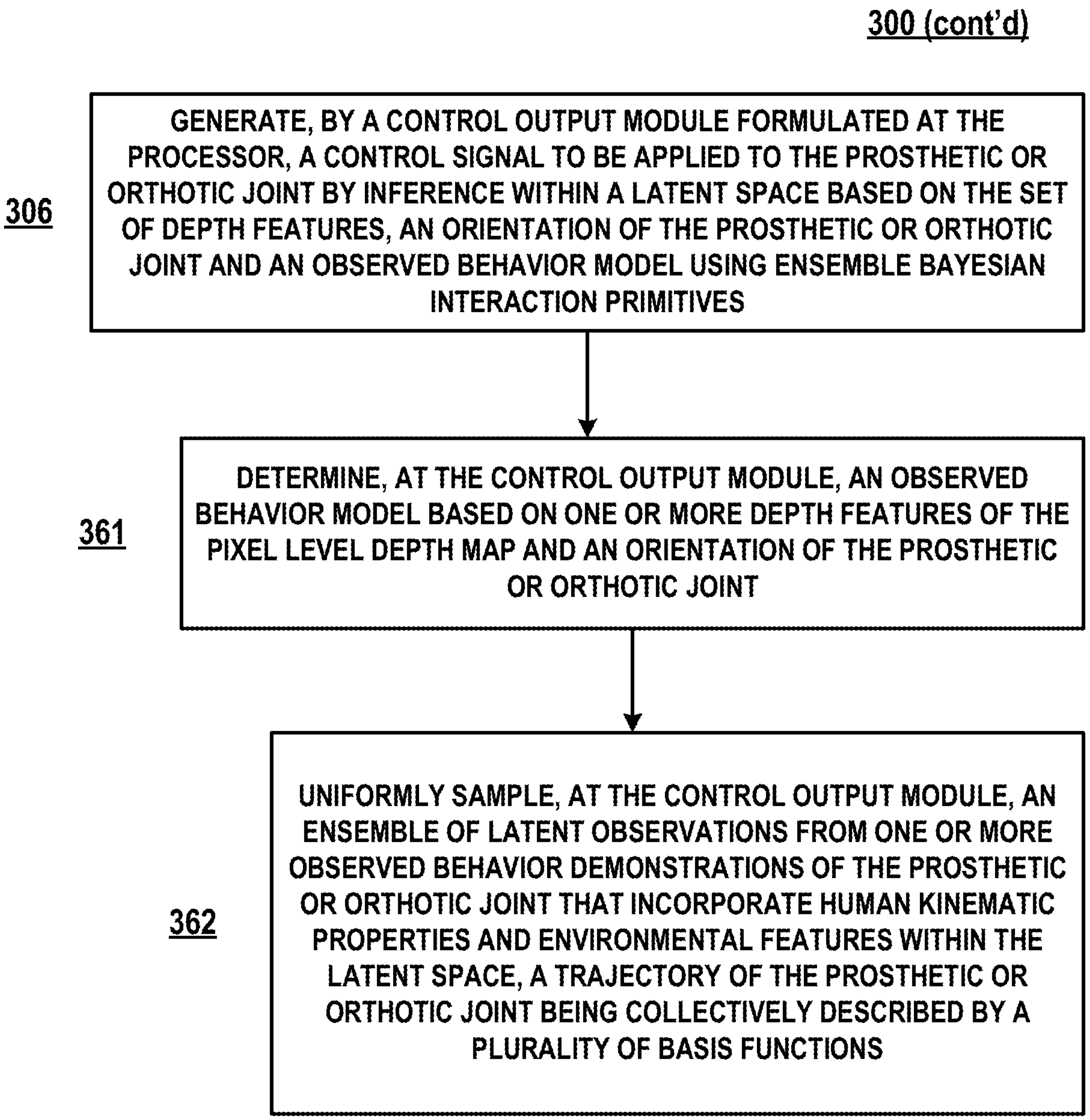

With reference to FIG. 11C, block 306 includes a sub-block 361, at which the processor determines, at the control output module, an observed behavior model based on one or more depth features of the pixel level depth map and an orientation of the prosthetic or orthotic joint. Sub-block 361 includes a further sub-block 362 at which the processor samples, at the control output module, an ensemble of latent observations from one or more observed behavior demonstrations of the prosthetic or orthotic joint that incorporate human kinematic properties and environmental features within the latent space, a trajectory of the prosthetic or orthotic joint being collectively described by a plurality of basis functions.

Figure 11D:
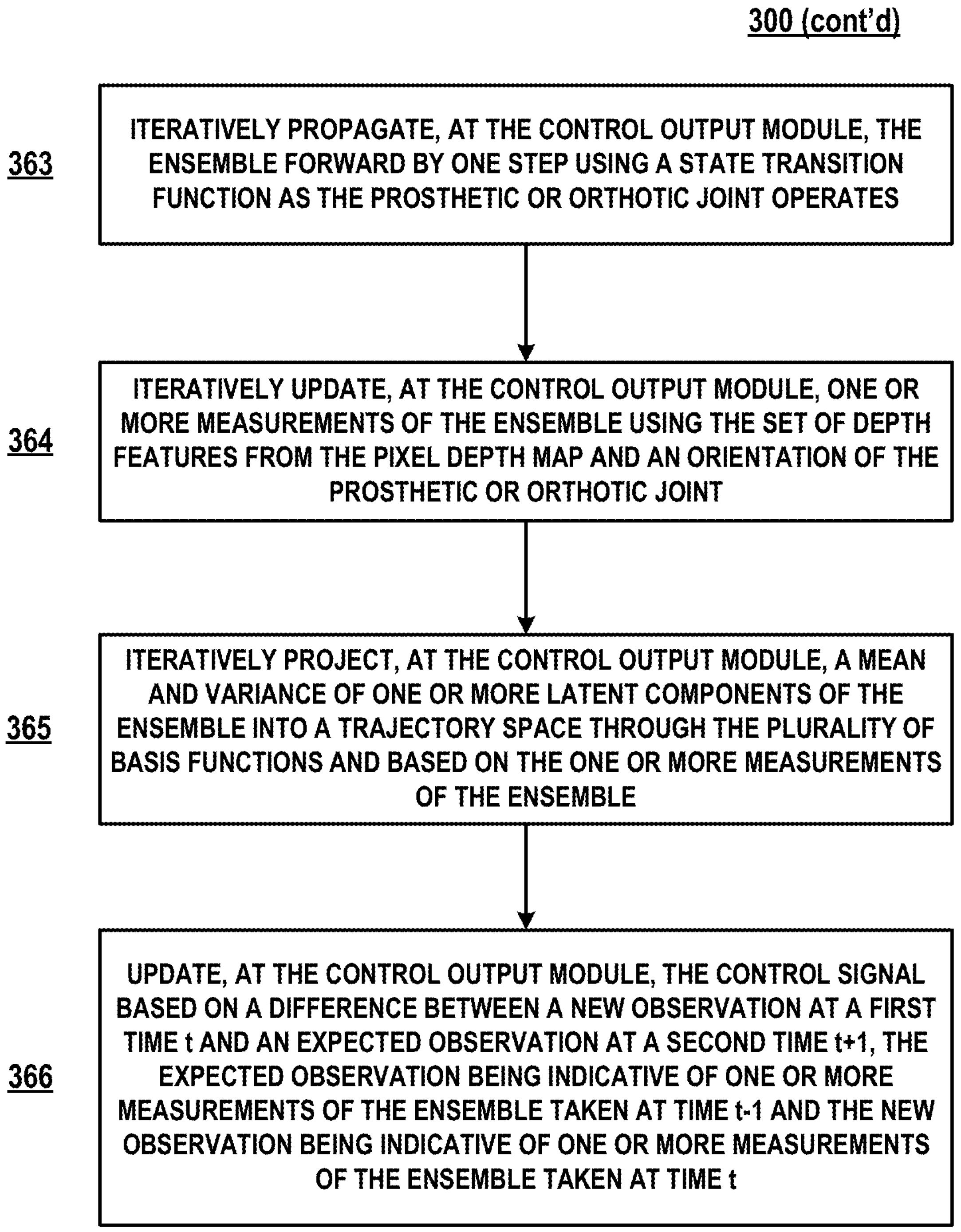

Continuing with FIG. 11D, sub-block 363 includes iteratively propagating, at the control output module, the ensemble forward by one step using a state transition function as the prosthetic or orthotic joint operates. Sub-block 364 includes iteratively updating, at the control output module, one or more measurements of the ensemble using the set of depth features from the pixel depth map and an orientation of the prosthetic or orthotic joint. Sub-block 365 includes iteratively projecting, at the control output module, a mean and variance of one or more latent components of the ensemble into a trajectory space through the plurality of basis functions and based on the one or more measurements of the ensemble. Sub-block 366 includes updating, at the control output module, the control signal based on a difference between a new observation at a first time t and an expected observation at a second time t−1, the expected observation being indicative of one or more measurements of the ensemble taken at time t−1 and the new observation being indicative of one or more measurements of the ensemble taken at time t. This control signal can be applied to the prosthetic or orthotic joint at block 308 of FIG. 11A.

Figure 11E:
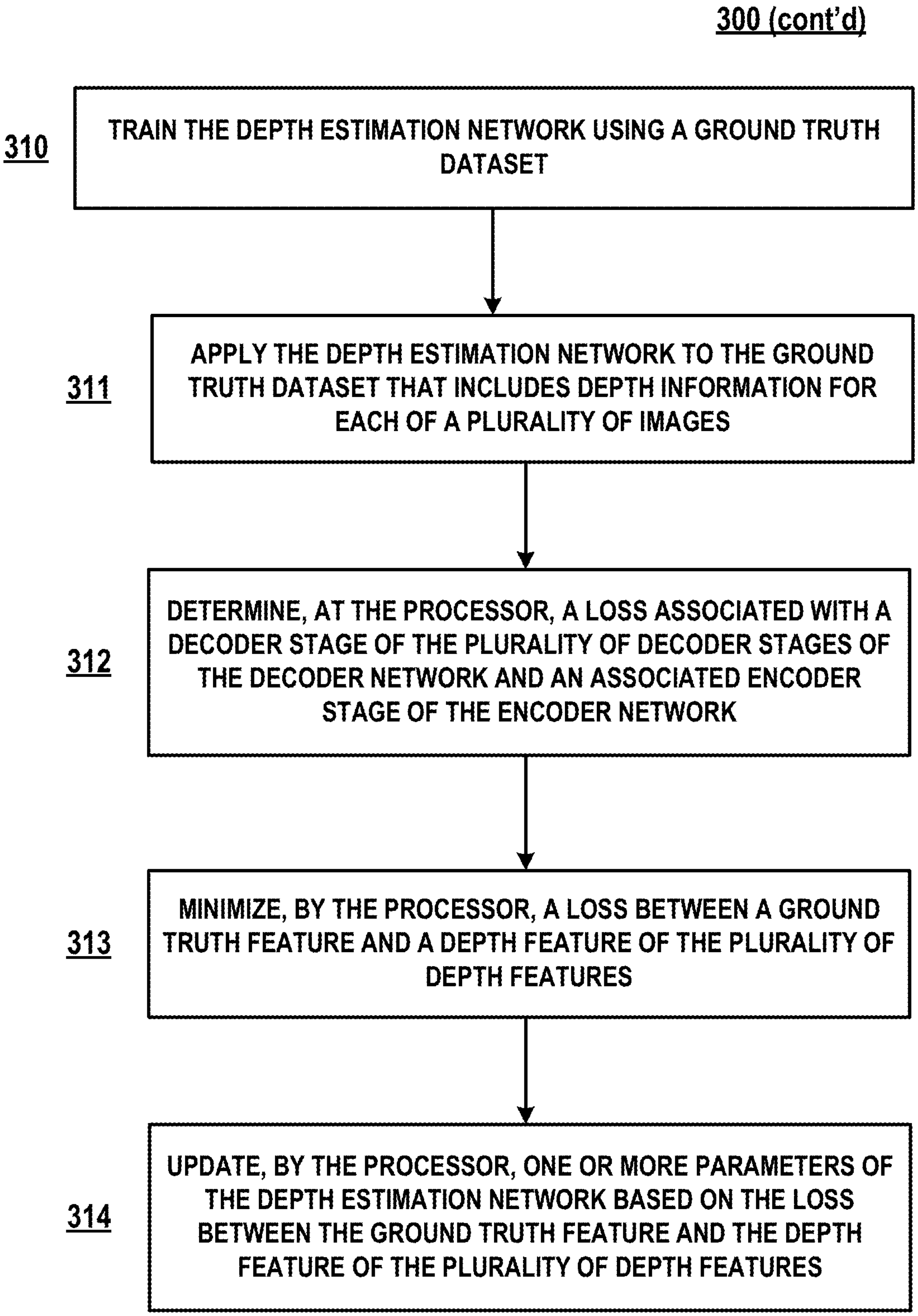

FIG. 11E shows training the depth estimation network using a ground truth dataset, which is outlined at block 310. At sub-block 311, the processor applies the depth estimation network to the ground truth dataset that includes depth information for each of a plurality of images. At sub-block 312, the processor determines, a loss associated with a decoder stage of a plurality of stages of the decoder network and an associated encoder stage of the depth estimation network. At sub-block 313, the processor minimizes a loss between a ground truth feature and a depth feature of the set of depth features. At block 314, the processor updates one or more parameters of the depth estimation network based on the loss between the ground truth feature and the depth feature of the set of depth features.

Figure 11F:
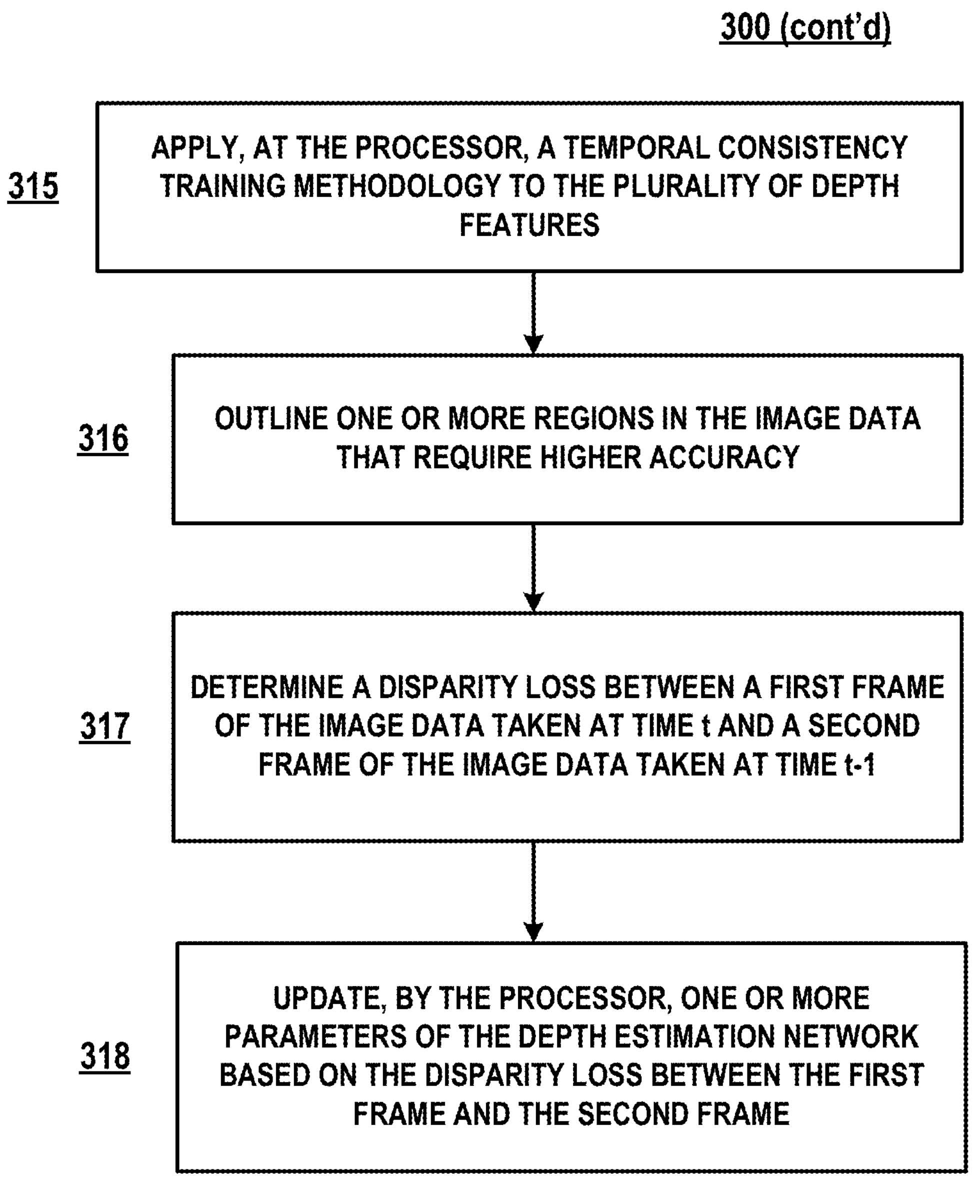

Continuing with FIG. 11F, at sub-block 315, the processor applies a temporal consistency training methodology to the set of depth features. Sub-block 315 can be divided further into sub-blocks 316, 317 and 318. At sub-block 316, the processor outlines one or more regions in the image data that require higher accuracy. At sub-block 317, the processor determines a disparity loss between a first frame of the image data taken at time t and a second frame of the image data taken at t−1. At sub-block 318, the processor updates one or more parameters of the depth estimation network based on the disparity loss between the first frame and the second frame.

Computer-Implemented System

Figure 12:
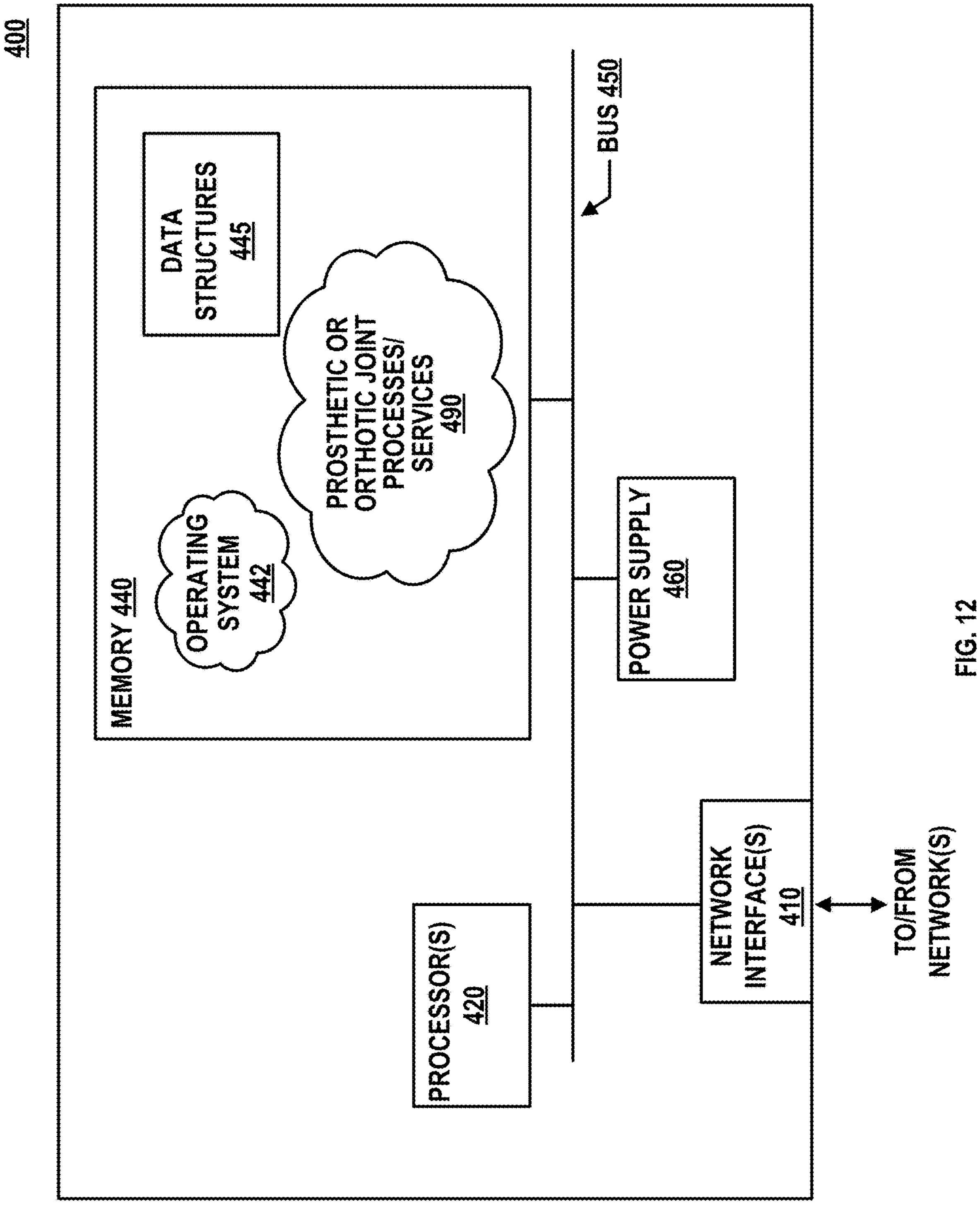
FIG. 12 is a simplified diagram showing an exemplary computing system for implementation of the system of FIG. 1.

FIG. 12 is a schematic block diagram of an example computing device 400 that may be used with one or more embodiments described herein, e.g., as a component of system 100 and/or implementing aspects of framework 200 in FIGS. 2A-2D and/or method 300 in FIGS. 11A-11F.

Device 400 comprises one or more network interfaces 410 (e.g., wired, wireless, PLC, etc.), at least one processor 420, and a memory 440 interconnected by a system bus 450, as well as a power supply 460 (e.g., battery, plug-in, etc.).

Network interface(s) 410 include the mechanical, electrical, and signaling circuitry for communicating data over the communication links coupled to a communication network. Network interfaces 410 are configured to transmit and/or receive data using a variety of different communication protocols. As illustrated, the box representing network interfaces 410 is shown for simplicity, and it is appreciated that such interfaces may represent different types of network connections such as wireless and wired (physical) connections. Network interfaces 410 are shown separately from power supply 460, however it is appreciated that the interfaces that support PLC protocols may communicate through power supply 460 and/or may be an integral component coupled to power supply 460.

Memory 440 includes a plurality of storage locations that are addressable by processor 420 and network interfaces 410 for storing software programs and data structures associated with the embodiments described herein. In some embodiments, device 400 may have limited memory or no memory (e.g., no memory for storage other than for programs/processes operating on the device and associated caches).

Processor 420 comprises hardware elements or logic adapted to execute the software programs (e.g., instructions) and manipulate data structures 445. An operating system 442, portions of which are typically resident in memory 440 and executed by the processor, functionally organizes device 400 by, inter alia, invoking operations in support of software processes and/or services executing on the device. These software processes and/or services may include prosthetic or orthotic joint processes/services 490 described herein. Note that while prosthetic or orthotic joint processes/services 490 is illustrated in centralized memory 440, alternative embodiments provide for the process to be operated within the network interfaces 410, such as a component of a MAC layer, and/or as part of a distributed computing network environment.

It will be apparent to those skilled in the art that other processor and memory types, including various computer-readable media, may be used to store and execute program instructions pertaining to the techniques described herein. Also, while the description illustrates various processes, it is expressly contemplated that various processes may be embodied as modules or engines configured to operate in accordance with the techniques herein (e.g., according to the functionality of a similar process). In this context, the term module and engine may be interchangeable. In general, the term module or engine refers to model or an organization of interrelated software components/functions. Further, while the prosthetic or orthotic joint processes/services 490 is shown as a standalone process, those skilled in the art will appreciate that this process may be executed as a routine or module within other processes.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A system, comprising:

a prosthetic or orthotic joint configured to receive one or more control signals and operate in response to the one or more control signals;

a camera that captures image data indicative of a surrounding environment around the prosthetic or orthotic joint; and a computing device in operative communication with the prosthetic or orthotic joint and the camera, the computing device including a processor in communication with a memory, the memory including instructions, which, when executed, cause the processor to:

receive, at the processor, the image data from the camera;

extract, by a depth estimation network formulated at the processor, a set of depth features indicative of perceived spatial depth information of a surrounding environment from the image data; and generate, by a control output module formulated at the processor, a control signal to be applied to the prosthetic or orthotic joint based on the set of depth features wherein the memory further includes instructions, which, when executed, cause the processor to:

uniformly sample, at the control output module, an ensemble of latent observations from one or more observed behavior demonstrations of the prosthetic or orthotic joint that incorporate human kinematic properties and environmental features within the latent space, a trajectory of the prosthetic or orthotic joint being collectively described by a plurality of basis functions;

iteratively propagate, at the control output module, the ensemble forward by one step using a state transition function as the prosthetic or orthotic joint operates;

iteratively update, at the control output module, one or more measurements of the ensemble using the set of depth features and an orientation of the prosthetic or orthotic joint;

iteratively project, at the control output module, a mean and variance of one or more latent components of the ensemble into a trajectory space through the plurality of basis functions and based on the one or more measurements of the ensemble; and update, at the control output module, the control signal based on a difference between a new observation at a first time t and an expected observation at a second time t−1, the expected observation being indicative of one or more measurements of the ensemble taken at time t−1 and the new observation being indicative of one or more measurements of the ensemble taken at time t.

2. The system of claim 1, wherein the memory further includes instructions, which, when executed, cause the processor to:

estimate, by the depth estimation network, a pixel level depth map from the image data captured by the camera.

3. The system of claim 2, wherein the memory further includes instructions, which, when executed, cause the processor to:

segment, by a segmentation module formulated at the processor and in communication with the depth estimation network, the pixel level depth map into a first area and a second area, the first area including a limb associated with the prosthetic or orthotic joint and the second area including an environment around the limb.

4. The system of claim 2, wherein the memory further includes instructions, which, when executed, cause the processor to:

determine, at the control output module, the control signal for the prosthetic or orthotic joint based on the pixel level depth map and an observed behavior model.

5. The system of claim 4, wherein the memory further includes instructions, which, when executed, cause the processor to:

determine, at the control output module, the observed behavior model based on one or more depth features of the pixel level depth map and an orientation of the prosthetic or orthotic joint.

6. The system of claim 5, further comprising:

an inertial measurement unit in communication with the control output module that determines the orientation of the prosthetic or orthotic joint.

7. The system of claim 1, wherein the memory further includes instructions, which, when executed, cause the processor to:

generate, at the control output module, one or more control signals by inference within a latent space based on the set of depth features and using ensemble Bayesian interaction primitives.

8. The system of claim 1, wherein the image data captured by the camera includes RGB image data, wherein each pixel of a plurality of pixels within the image data includes a corresponding RGB value.

* * * * *